(12) United States Patent  (10) Patent No.: US 8,029,576 B2
Noecker et al.  (45) Date of Patent: Oct. 4, 2011

(54) COMPOSITION FOR DYEING KERATIN FIBRES

(75) Inventors: Bernd Noecker, Ober-Ramstadt (DE); Jonathan Wood, Weinheim (DE); Ruediger Wilz, Pfungstadt (DE); Frank Kufner, Darmstadt (DE)

(73) Assignee: KPSS-KAO Professional Salon Services GmbH, Darmstadt (DE)

( * ) Notice: Subject to any disclaimer, the term of this patent is extended or adjusted under 35 U.S.C. 154(b) by 635 days.

(21) Appl. No.: 12/056,100

(22) Filed: Mar. 26, 2008

(65) Prior Publication Data

US 2008/0216253 A1  Sep. 11, 2008

Related U.S. Application Data

(63) Continuation-in-part of application No. 11/133,590, filed on May 20, 2005, now abandoned, and a continuation-in-part of application No. 11/133,495, filed on May 20, 2005, now abandoned, and a continuation-in-part of application No. 11/133,494, filed on May 20, 2005, now abandoned, and a continuation-in-part of application No. 11/133,525, filed on May 20, 2005, now abandoned, and a continuation-in-part of application No. 11/133,496, filed on May 20, 2005, now abandoned.

(30) Foreign Application Priority Data

May 22, 2004 (EP) .................... 04012174
May 22, 2004 (EP) .................... 04012175
May 22, 2004 (EP) .................... 04012176
May 22, 2004 (EP) .................... 04012177
May 22, 2004 (EP) .................... 04012178

(51) Int. Cl.
    *A61Q 5/10*    (2006.01)
(52) U.S. Cl. ............. 8/405; 8/406; 8/407; 8/409; 8/410; 8/411; 8/421; 8/426; 8/455; 8/466; 8/516; 8/552; 8/632
(58) Field of Classification Search ............. 8/405, 406, 8/407, 409, 410, 411, 421, 426, 455, 466, 8/516, 552, 632
See application file for complete search history.

(56) References Cited

U.S. PATENT DOCUMENTS 5,188,639 A    2/1993   Schultz et al.
5,618,525 A *  4/1997   Bunning .................. 424/70.122
6,001,135 A    12/1999  Rondeau et al.
6,099,592 A    8/2000   Vidal et al.
6,616,707 B2   9/2003   Lorenz
6,743,263 B1   6/2004   Hoeffkes et al.
2002/0139957 A1* 10/2002 Matsuo et al. ............. 252/186.1
2003/0159221 A1  8/2003  Lang

FOREIGN PATENT DOCUMENTS

EP    1166752 A2      1/2002
FR    2845283 A       4/2004
WO    9936037 A       7/1999
WO    02074270 A1     9/2002
WO    03/022232 A2    3/2003
WO    03/076518 A2    9/2003
WO    WO 03/076518 A2 *  9/2003

OTHER PUBLICATIONS

English Language Abstract for EP1166752, (Feb. 2002).
English Language Abstract for FR 2845283, (Sep. 2004).

* cited by examiner

*Primary Examiner* — Eisa Elhilo
(74) *Attorney, Agent, or Firm* — Norris McLaughlin & Marcus, P.A.

(57) ABSTRACT

This invention relates to a hair dyeing composition comprising at least one anionic and at least one cationic direct acting hair dyes and showing excellent dyeing ability and excellent resistance to hair washing and environmental influences. The coloring composition of this invention are ready to use coloring composition and, therefore, do not require any mixing prior to application with additional agents such as oxidizers. According to the invention the preferred cationic dyestuffs are selected from the following structures

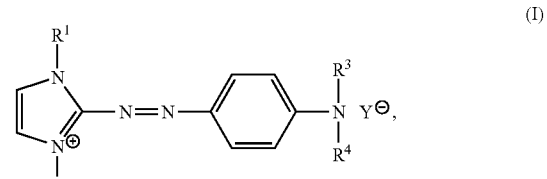

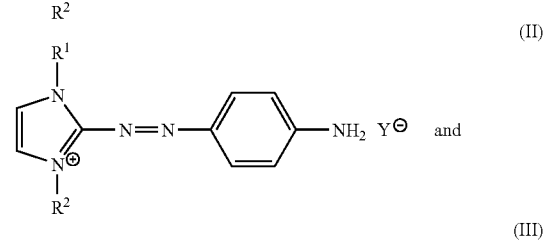

wherein $R^1$, $R^2$, $R^3$ and $R^4$ stand for hydrogen, a $CH_3$— or $C_2H_5$— group, and Y is an anion such as chloride, bromide, methosulfate.

30 Claims, No Drawings

COMPOSITION FOR DYEING KERATIN FIBRES

This application is a continuation-in-part application of U.S. application Ser. No. 11/133,590 (ABN), filed May 20, 2005 which claims the benefit of European Patent Application No. 04012174.1, filed May 22, 2004; U.S. application Ser. No. 11/133,495 (ABN), filed May 20, 2005 which claims the benefit of European Patent Applications 04012174.1 and 04012175.8 filed May 22, 2004; U.S. application Ser. No. 11/133,494 (ABN), filed on May 20, 2005 which claims the benefit of European Patent Application No. 04012176.6 filed on May 22, 2004; U.S. application Ser. No. 11/133,525 (ABN), filed May 20, 2005 which claims the benefit of European Patent Application 04012177.4 filed May 22, 2004; and U.S. application Ser. No. 11/133,496 (ABN)filed May 20, 2005 which claims the benefit of European Patent Application 04012178.2 filed May 22, 2004.

This invention relates to a dyeing composition for keratin fibres, especially hair, comprising at least one anionic and at least one cationic direct acting hair dyes and showing excellent dyeing ability and excellent resistance to hair washing and environmental influences. The colouring composition of this invention are ready to use colouring composition and, therefore, do not require any mixing prior to application with additional agents such as oxidizers.

In another way of carrying out the invention and in the case that a brightening and lightening, in hair colour, are wished, the compositions of the present invention can as well be used after mixing with an oxidizing agent.

Hair colouring is a common practice for ages. Oxidative colouration has widely been used for achieving durable, brilliant hair colour. Direct dyes, mainly of cationic character, have also found their applications for colouring hair. Recently, anionic direct dyes have as well been found to be very powerful for changing hair colour permanently and to achieve long lasting, brilliant colours in strong acidic medium. The colouring agents with anionic dyes are so formulated that the optimum conditions are realised for achieving the highest dyestuff penetration into hair. European patent application with laid open number EP 1 022 014 describes such compositions comprising anionic dyestuffs, solvents, as aid to enhance penetration of said dyestuffs, and a buffer solution to adjust the pH of the dyeing agent in the range from 2 to 6. For enhancing penetration of dyestuffs, solvents are used such as ethanol, benzyl alcohol, propylene carbonate, dipropylene glycol. Products are found on the professional hair dressing market applying this technology.

U.S. Pat. No. 5,601,620, as well, discloses hair colouring agents with acid dyes, an organic solvent and at least one polysiloxane as a conditioner. The dyeing compositions disclosed here are having a pH in the range of 1.5-4.5.

Above two documents deal with the anionic dyes in acidic medium and they are silent on any colouring and/or lightening compositions at an alkaline pH and optionally comprising an oxidizing agent.

In an earlier European Patent application from our company with the application number 04 001 799.8, hair colouring composition is disclosed based on only anionic acidic direct dyes at alkaline medium. In that application, the possibility of addition of cationic dyestuff is disclosed to be only at minor quantities, preferably is not advised.

EP 810 851, on contrary to the above two publications, discloses hair colouring and lightening compositions comprising a cationic direct dye and an oxidizing agent. This documents is totally silent on any composition comprising anionic dyes.

In practice, further development is obviously desired by professional hair dressing practitioners and also by end consumers in order to achieve highly brilliant and long lasting colorations. Additionally, colour resistance against washing and environmental influences is highly desirable. Furthermore, partial colourations in form of streaks has become popular and products are desired showing optimal colouring and at the same time optimal lightening performance for colourful hair appearance.

This invention starts with the above mentioned problems and discloses primarily a hair colouring and secondarily a lightening composition with excellent colouring and highlighting effects together with excellent stability against washing (shampooing) and environmental influences.

Inventors of the present invention have surprisingly been found out that hair colouring compositions on aqueous basis comprising at least one direct acting anionic dyestuff and at least one direct action cationic dyestuff show excellent colouring ability and excellently stable against washing (shampooing) and environmental influences. Additionally, colouring compositions of the present invention are excellently suitable for lightening and colouring purposes when mixed with an oxidizing agent prior to application.

According to the invention the suitable direct acting anionic dyes are:

Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Among those, the most preferred anionic dyestuffs are Acid Red 52, DC Violet 2, DC Red 33, DC Orange 4, DC Red 27 and DC Yellow 10.

According to the invention, suitable cationic dyestuffs are in principal those available on the market for cosmetic hair colouring applications. For this purpose, special reference is made to the PCT application WO 95/15144 of Ciba-Geigy AG.

The cationic dyestuffs with the following chemical structures are especially, the most preferred ones according to the present invention.

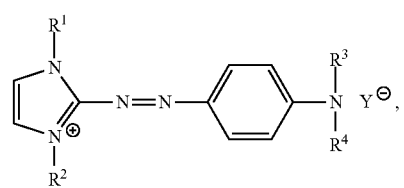
(I)

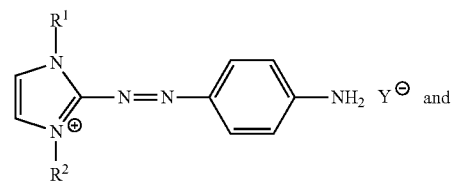
(II)

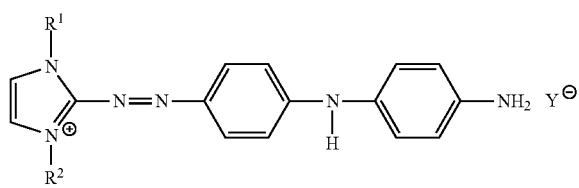
(III)

wherein $R^1$, $R^2$, $R^3$ and $R^4$ stand for hydrogen, a $CH_3$— or $C_2H_5$— group, and Y is an anion such as chloride, bromide, methosulfate.

The most preferred compounds are the ones according to the formula I, where $R_1$, $R_2$, $R_3$ and $R_4$ are methyl and Y is chloride and according to formula II where $R_1$ and $R_2$ are methyl and Y is chloride.

Additionally other cationic dyestuffs can as well be used in addition to the cationic dyestuffs mentioned above. Some examples to those are:
Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14 and Basic Yellow 57.

According to the invention, coloring composition comprises anionic dyes at a concentration of 0.1 to 7.5%, preferably 0.2 to 5%, more preferably 0.2 to 3% by weight calculated to total composition. Cationic dyestuffs are included into the compositions of the present invention at a concentration of 0.01 to 2.5%, preferably 0.05 to 2% and more preferably 0.05 to 1% by weight calculated to total composition.

Interestingly it has as well been found out that the ratio of acidic dyes to cationic dyes plays an important role for achieving especially resistance to washing and environmental effects.

Accordingly, the ratio of cationic dyestuffs to acidic dyestuffs by weight is in the range of 3:1 to 1:10, preferably 2:1 to 1:7 and further more preferably 2:1 to 1:5.

Additionally, the coloring compositions of the present invention may comprise neutral dyes (HC dyes), so called nitro dyes for shading purposes. Concentration of those can typically be in the range from 0.01 to 2.5%, preferably 0.1 to 2% by weight calculated to total composition.

Some examples to those are: HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 1, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder, etc.

pH of the coloring compositions of the present invention varies between 5 and 12, preferably 6-11, more preferably 6.8 to 10. In the case that, the composition is used for highlighting (lightening) and coloring, the forgoing pH values refer to the pH of the dyeing composition before mixing with oxidizing agent. pH of the colouring composition is adjusted to the required pH by using triethanolamine, ammonia or its salts with acids such as ammonium chloride, ammonium sulphate, ammonium carbonate, ammonium bicarbonate, ammonium nitrate, or using alkaline solutions such as sodium hydroxide, potassium hydroxide and their respective salts with the known acids.

Colouring composition of present invention can comprise additionally in the base formulation fatty acids with 0 to 3 ethylenic bonds and with fatty acyl chain length of 12 to 22 C atom. Concentration of the fatty acids can be in the range of 0.1 to 10%, preferably 0.1 to 7.5% and most preferably 0.2 to 5% by weight calculated to the total composition. Fatty acid examples, without limiting the choice, suitable for colouring compositions are myristic acid, palmitic acid, behenic acid, steraic acid, oleic acid, linoleic acid. The most preferred fatty acid is oleic acid.

Colouring compositions according to the present invention can be in the form of emulsion, solution, dispersion and/or gel. Emulsion form is preferred.

In the case that the colouring composition is in the form of an emulsion, it comprises as an emulsion base at least one fatty alcohol or mixture of fatty alcohols with the chain length of 14 to 22 C atoms. Examples to suitable fatty alcohols, without limiting the choice, are myristyl alcohol, cetyl alcohol, stearyl alcohol, behenyl alcohol and cetostearyl alcohol. The most preferred is cetostearyl alcohol well known with its trade name Lanette O or as Lanette N in mixture with sodium cetearyl sulfate from Cognis.

The concentration of fatty alcohol(s) is in the range from 0.5 to 20%, preferably 0.5 to 15% by weight, calculated to total composition.

Colouring compositions according to present invention comprises surfactants selected from anionic, nonionic, amphoteric (or zwitterionic) and/or cationic surfactants as emulsifier or solubilizer. Cationic surfactants are as well used as hair conditioners in the colouring composition.

Anionic surfactants suitable within the scope of the invention are in principal known from the cleansing compositions and are preferably present in an amount from 0.1 to about 10%, preferably 0.2 to 7.5% and most preferably 0.2-5% by weight, calculated to the total composition.

These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula $$R_5-(C_2H_4O)_n-O-CH_2COOX,$$

wherein $R_5$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

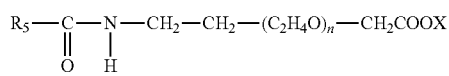

wherein $R_5$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular in admixture with the above-named anionic surfactants.

It is also possible to use mixtures of several anionic surfactants in a mixture.

An overview of the anionic surfactants suitable for the present invention can furthermore be found in the monography of K. Schrader, "Grundlagen und Rezepturen der Kosmetika", $2^{nd}$ Ed. (1989, Hüthig Buchverlag), pp. 595-600 and pp. 683 to 691.

Further surfactants in the colouring compositions according to the invention are nonionic surfactants alone or in admixture with anionic surfactants at a weight ratio of 3:1 to 1:3.

These are described as well in Schrader, l. c., on pages 600-601 and pp. 694-695.

Especially suited nonionic surfactants are, for example, long-chain fatty acid mono- and dialkanolamides, such as coco fatty acid mono- or diethanolamide and myristic fatty acid mono or diethanolamide, stearic acid mono or diethanolamide.

Further nonionic surfactants suited are alkyl polyglucosides of the general formula $$R_6-O-(R_3O)_n-Z_x,$$

wherein $R_6$ is an alkyl group with 8 to 18 carbon atoms, $R_3$ is an ethylene or propylene group, Z is a saccharide group with 5 to 6 carbon atoms, n is a number from 0 to 10 and x is a number between 1 and 5.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are amineoxides. Such amineoxides are state of the art, for example $C_{12}$-$C_{18}$-alkyl dimethyl amineoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl)amineoxides, or also amineoxides with ethyleneoxide and/or propyleneoxide groups in the alkyl chain. Such amineoxides are on the market, for example, under the trade names "Ammonyx®", "Aromox®" or "Genaminox®".

Further nonionic surfactants useful in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

As further surfactant component, the colouring compositions according to the invention can also contain amphoteric or zwitterionic surfactants, for example in an amount from about 0.5% to about 5%, preferably from about 1% to about 2.5% by weight, calculated to the total composition.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

In detail, it is possible to use betaines of the structures

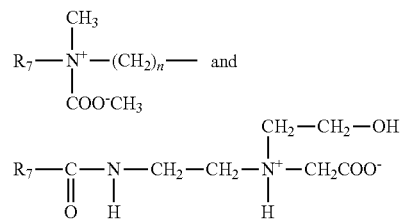

wherein $R_7$ is a $C_8$-$C_{18}$-alkyl group and n is 1 to 3; sulfobetaines of the structure

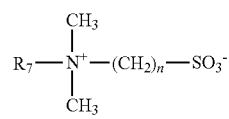

wherein $R_7$ and n are same as above; and amidoalkyl betaines of the structure

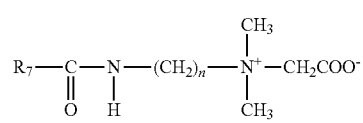

wherein $R_7$ and n are same as above.

Colouring composition can contain cationic surfactants as emulsifier, solubilizer and/or conditioning ingredients according to the formula, but not limited to.

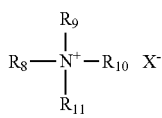

where $R_8$ is a saturated or unsaturated, branched or non-branched alkyl chain with 8-22 C atoms or

where $R_{12}$ is saturated or unsaturated, branched or non-branched alkyl chain with 7-21 C atoms and n has typical value of 1-4 or

where $R_{13}$ is saturated or unsaturated, branched or non-branched alkyl chain with 7-21 C atoms and n has typical value of 1-4, and $R_9$ is H or unsaturated or saturated, branched or non-branched alkyl chain with 1-22 C atoms or

or

where $R_{12}$, $R_{13}$ and n are same as above.

$R_{10}$ and $R_{11}$ are H or lower alkyl chain with 1 to 4 Carbon atoms, and X is typically chloride, bromide, methosulfate.

Typical examples of those ingredients are cetyl trimethly ammonium chloride, stear trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

Colouring composition can also contain cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46. Among those the most preferred one is the Polyquaternium 11 as well known with its trade name Gafquat from ISP and as Luviquat PQ from BASF.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

Typical concentration range for any of the cationic conditioners mentioned above can be 0.01-5% by weight, preferably 0.03-2.5% by weight and more preferably 0.05-1.5% by weight.

Hair dyeing composition of the present invention preferably comprise an organopolysiloxane wherein at least one silicium atom is linked to an alkylene group having a heteroatom, in particular a nitrogen atom, with a poly-(N-acyl alkyleneimine) units of the formula

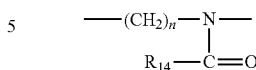

wherein n is a number from 1 to 5 and $R_{14}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

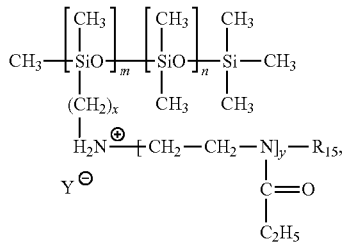

wherein m and n each are numbers from 20 to 10,000, in particular 50 to 7,000, especially 100 to 5,000, x is a number between 1 and 5, preferably 3, and y is a number from 5 to 30, $R_{15}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Colouring compositions according to the present invention can contain organic solvents as penetration enhancers and also as a solubilzers. Examples of such organic solvents are benzyloxy ethanol, benzyl alcohol, phenoxy ethanol, phenoxy isopropanol, methyl phenoxy ethanol, benzyl glycerol, N-benzyl formide, N-methylpyrrolidone, N-ethyl pyrrolidone, cinnamyl alcohol, phenethyl alcohol, p-methyl benzyl alcohol, butyl cellosolve, methyl carbitol, ethyl carbitol, propyl carbitol, butyl carbitol, diethyleneglycol, diethyl ether and dipropyleneglycol diethyl ether. Typically the concentration of those solvents can be in the range from 0.5% to 10%, preferably 0.5-5% by weight calculated to the total composition.

The hair dyeing compositions according to the invention preferably contain thickening agents. These are, for example, the various cellulose derivatives such as hydroxyalkyl celluloses, e.g. hydroxyethyl cellulose, hydroxypropyl cellulose, hydroxypropyl methyl cellulose, natural polysaccharides such as xanthan gum; guar gum and the alkoxylation products thereof in amounts from 0.1-5%, preferably 0.1-3% and most preferably 0.1-2% by weight calculated to the total composition and depending on the desired consistency thereof.

Optionally, the colouring composition of this invention can comprise further hair conditioning agents such as silicone oils either volatile or non-volatile, natural and synthetic oils. Among silicone oils those can be added to the colouring composition include dimethicone, dimethiconol, polydimethylsiloxane, DC fluid ranges from Dow Corning, natural oils such as olive oil, almond oil, avocado oil, weizenkeim oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate.

Additional non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula X or XI, respectively,

$R_{16}CO(OCH_2CH_2)_nOH$          formula X

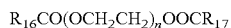

$R_{16}CO(OCH_2CH_2)_nOOCR_{17}$          formula XI where $R_{16}$ and $R_{17}$ are independent from each other saturated, unsaturated or branched or non-branched alkyl chain with 7 to 21 C atoms and n is typically 2-100.

Another preferred compound in the colouring composition is of ceramide type of compounds according to general formula

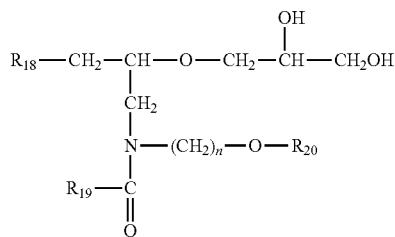

where $R_{18}$ and $R_{19}$ are independent from each other alkyl- or. alkenyl group mit 10 to 22 carbon atoms, $R_{20}$ is methyl, ethyl, n-propyl or isopropyl group and n is a number between 1 to 6, preferably 2 or 3. The concentration of ceramide type of compound in colouring compositions of the present invention can be in the range of 0.01 to 2 and especially 0.01 to 1% by weight calculated to the total composition.

Colouring composition may as well contain UV filters of oil soluble, non-ionic, ones and/or as well those of water soluble and mainly of anionic character. Examples are Benzophenone-1 Benzophenone-2, Benzophenone-3, Benzophenone-7, Benzophenone-6, Benzophenone-8, octylmethoxy cinnamate, homosalat to those of oil soluble ones and Benzophenone-4, benzophenone-9 to those anionic water soluble ones. It should be noted that the other UV filters of oil and water soluble ones should as well be possible to combine.

Another preferred way of carrying out the present invention is that mixing colouring compositions with a composition comprising at least one oxidizing agent prior to application onto hair. By doing so, lightening (highlighting) and colouring is achieved at the same time. In another words, original hair colours is lightened and at the same time dyes, stable in the presence of oxidizing agent, are deposited onto hair so that new colour appearance is achieved. The oxidizing agents suitable are hydrogen peroxide, urea peroxide, melamin peroxide or perborate salts. The most preferred is hydrogen peroxide, which is used as a lotion containing 3 to 12% by weight, calculated to composition only comprising hydrogen peroxide.

The new composition as a result of mixing colouring and oxidizing composition allows achieving simultaneous lightening and colorations. The mixing ratio of the colouring composition and oxidizing composition should be in the range of 4:1 to 1:4, by weight, preferably 2:1 to 1:3 by weight.

Colouring and highlighting with compositions of the present invention can be carried out in different ways of processing.

One of the processes is that colouring composition is mixed with an oxidizing composition and applied onto hair and after a processing time, depending on the wished lightening and as well colour tone, processed for 5 to 45 min and rinsed off from hair.

Another way of carrying out highlighting and colouring is that of two step application. In the first step, composition comprising at least one oxidizing agent is applied onto hair and left on the hair for 5 to 45 min and without rinsing off, the colouring agent is applied onto hair as a second step and after leaving onto hair additional 5 to 45 min the mixed compositions are rinsed of from hair.

In the above mentioned two step colouring and highlighting process, between the application of first and second agents, the hair can be washed with water and optionally hair can be dried.

In the lightening and colouring process using the colouring composition of the present invention, the lightening can as well be carried out with the composition known as bleaching agents. For such a process suitable bleaching composition is for example the one disclosed in a European Patent No 560 088. Preferred way of carrying out lightening an colouring using bleaching agents is two step process as mentioned above.

Another way of carrying out the invention is that addition of oxidation dyestuffs precursors (developing substances) and coupling substances into the colouring compositions of the present invention. Those oxidative dyes can as well be mixed into the colouring composition prior to application onto hair. It is possible to incorporate developing substances known per se. In the case of oxidation dyes are present in the compositions, colouring is than carried out in the presence of oxidizing agent, i.e. oxidative dye containing colouring composition is mixed with oxidizing agent prior to application. Special mention is made of p-phenylenediamine, p-methylaminophenol and substituted p-phenylenediamines such as 2,5-diamino-toluene, 2-n-propyl or 2-ethyl-p-phenylenediamine, 2,6-di-methyl-p-phenylene-diamine, 2-(2,5-diaminophenyl)ethanol, 1-amino-4-bis-(2'-hydroxy-ethyl)aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetramino pyrimidines, triaminohydroxy pyrimidines, diaminomono- and -dihydroxy pyrimidines, aminotriazines, 5-amino salicylic acid and/or 1,2,4-triamino benzene or the water-soluble salts thereof.

Further suitable aminopyridines are 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethylpyridine, 2-amino-3-hydroxypyridine, 3-amino-2 (β-hydroxyethyl amino)-6-methoxy-pyridine, 2,6-dimethyl amino-5-aminopyridine, 2-di(hydroxyethyl)amino-5-aminopyridine, 2-hydroxyethyl amino-5-aminopyridine, 4-hydroxy-2,5,6-triaminopyrimidine and/or the water-soluble salts thereof.

The total concentration of the developing substances customarily ranges between about 0.05% and 5%, preferably 0.1% and 4%, in particular 0.1% to 3% by weight, calculated to the total hair dyeing composition (excluding the oxidation agent), whereby these figures are always related to the proportion of free base.

The composition according to the present invention can contain coupling substances, which can be selected from 5-amino-2-methylphenol, 2-methyl-5-hydroxyethylaminophenol, 2,4-diaminophenoxyethanol, 2-amino-4-hydroxyethylaminoanisol, 2-methyl-5-amino-6-chlorophenol, 1,3-bis(2,4-diaminophenoxy)propane, 2-bis(2-hydroxyethyl) aminotoluene, 2-amino-5-methylphenol, resorcinol, 2-methyl resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 1,3-diamino-benzene, 1-amino-3-(2'-hydroxyethylamino)benzene, 1-amino-3-[bis(2'-hydroxyethyl)amino]benzene, α-naphthol, 4,6-dichlororesorcinol, 1,3-diamino-toluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof.

Further, Indole and indoline derivatives can as well be contained in the colouring composition of the present invention. Examples to those are: 6-aminoindol, 6-hydroxyindole, 1-ethyl-6-hydroxyindole, 1-methyl-4-hydroxyindol, 1-methyl-6-hydroxyindole, 2-methyl-6-hydroxyindole, 5-hydroxyindol, 4-hydroxyindol, 5,6-dihydroxyindole, 6-aminoindoline, 6-hydroxyindoline, 1-ethyl-6-hydroxyindoline, 1-methyl-4-hydroxyindoline, 1-methyl-6-hydroxyindoline, 2-methyl-6-hydroxyindoline, 5-hydroxyindoline, 4-hydroxyindoline, 5,6-dihydroxyindoline and their respective salts.

In the hair dyeing compositions according to the invention, the coupling substance(s) as reaction partners of the developing substance(s) are present in approximately the same molecular proportions as the developing substances, i.e. in amounts from 0.01% to 5.0%, preferably 0.05% to 4%, in particular 0.1% to 3% by weight, calculated to the total composition (excluding the oxidizing agent), whereby these figures are always related to the proportion of free base.

The composition of the present invention can contain additional ingredients such as preservatives, chelating agents, fragrance and substances customarily used in cosmetic colouring compositions.

The viscosity of the compositions according to the invention preferably ranges from 1,000 to 50,000, in particular 1,000 to 30,000, especially 1,000 to 20,000 mPa·s, measured at 20° C. with a Brookfield rotation viscosimeter, with spindle 5 at 5 rpm.

The invention is illustrated with the following examples, but not limited to.

| Base formulations | % by weight I | % by weight II |
|---|---|---|
| Stearamide MEA | — | 1.50 |
| Cocamide MEA | 4.00 | 2.00 |
| Cetearyl alcohol | 10.00 | 8.00 |
| Tegin P | 1.40 | 1.40 |
| Propylene Glycol | 2.40 | 1.60 |
| Oleic acid | 3.00 | 3.00 |
| Ammonium chloride | 0.50 | 0.50 |
| Tetrasodium EDTA | 0.20 | 0.20 |
| Sodium lauryl sulfate | 1.50 | — |
| Sodium cetearyl sulfate | — | 1.20 |
| Organopolysiloxane A1 of EP 640 643 | 0.20 | 0.20 |
| Ceramide according to formula wherein $R_{18}$ and $R_{19}$ are C16 and $R_{20}$ is ethyl | — | 0.20 |
| Water | to 100 | to 100 |

The dyestuffs given in the following as for various color directions are added to the base compositions either I or II. Water amount is reduced in the base formula corresponding to the amount of dyes present in the formulations.

Dyestuff Composition Examples:

TABLE I

| | % by weight | |
|---|---|---|
| | Intensive red | Violet-red |
| Acid Red 52 | 1.50 | — |
| DC Violet 2 | — | — |
| DC Red 33 | — | 1.50 |
| DC Orange 4 | — | — |
| Dyestuff of formula I $R_1 = R_2 = R_3 = R_4$ = methyl | 0.50 | 0.50 |
| Base formula | I or II | I or II |

TABLE II

| | % by weight | |
|---|---|---|
| | Orange (reddish) | Intensive red |
| Acid Red 52 | — | 0.60 |
| DC Violet 2 | — | — |
| DC Red 33 | — | — |
| DC Orange 4 | 1.50 | — |
| Dyestuff of formula I $R_1 = R_2 = R_3 = R_4$ = methyl | 0.50 | 1.20 |
| Base formula | I or II | I or II |

TABLE III

| | % by weight | | |
|---|---|---|---|
| | Orange | orange-red | Violet-red |
| Acid Red 52 | — | 1.50 | — |
| DC Violet 2 | — | — | — |
| DC Red 33 | — | — | 1.5 |
| DC Orange 4 | 1.50 | — | — |
| Dyestuff of formula II $R_1 = R_2$ = methyl | 0.50 | 0.50 | 0.50 |
| Base formula | I or II | I or II | I or II |

The coloring compositions so obtained show excellent dyeing performance when applied as they are without premixing with any other composition.

In addition the coloring compositions are mixed with a solution comprising 12% by weight hydrogen peroxide at a ratio of 1:2 (coloring mass:peroxide solution) and applied onto hair, in all cases, excellent highlighting and coloring effects are observed.

In order show color fastness against washing, an intensive red colored hair tress with a composition comprising acid red 52 and cationic red dye according to formula I with $R_1=R_2=R_3=R_4$=methyl, as presented above, was washed 10 times under usual hair wash conditions with a commercial shampoo composition designed for colored hair of the trade mark Goldwell Definition, and color of the tresses (L, a and b values) were measured before and after shampooing optically with a laboratory equipment and color differences were calculated with the well known equation to obtain ΔE values and color intensity differences (ΔL) were obtained from measured L values. The results are presented in Table IV below. The test was as well carried out with compositions comprising only the cationic dyestuff of formula I with $R_1=R_2=R_3=R_4$=methyl, at a concentration as incorporated into the inventive coloring composition and at a concentration equal to the total dyestuff content of the inventive composition (sum of concentrations anionic and cationic dyestuffs).

TABLE IV

Results of durability test against wash - shampooing

|  | ΔE | ΔL |
|---|---|---|
| Inventive composition 0.5% cationic and 1.5% anionic dyestuffs | 6.1 | 2.9 |
| Comparative with 0.5% cationic dye | 13.5 | 8.1 |
| Comparative with 2% cationic dye | 10.1 | 5.1 |

The results in the table should be understood as the lower the value, the better the colourfastness against washing. Thus, the most stable color is obtained with the inventive composition.

This invention relates to a dyeing composition for keratin fibers, especially hair, comprising at least one anionic and at least one cationic direct acting hair dyes and showing excellent dyeing ability and excellent resistance to hair washing and environmental influences. The colouring composition of this invention are ready to use colouring composition and, therefore, do not require any mixing prior to application with additional agents such as oxidizers.

In another way of carrying out the invention and in the case that a brightening and lightening, in hair colour, are wished, the compositions of the present invention can as well be used after mixing with an oxidizing agent.

Hair colouring is a common practice for ages. Oxidative colouration has widely been used for achieving durable, brilliant hair colour. Direct dyes, mainly of cationic character, have also found their applications for colouring hair. Recently, anionic direct dyes have as well been found to be very powerful for changing hair colour permanently and to achieve long lasting, brilliant colours in strong acidic medium. The colouring agents with anionic dyes are so formulated that the optimum conditions are realised for achieving the highest dyestuff penetration into hair. European patent application with laid open number EP 1 022 014 describes such compositions comprising anionic dyestuffs, solvents, as aid to enhance penetration of said dyestuffs, and a buffer solution to adjust the pH of the dyeing agent in the range from 2 to 6. For enhancing penetration of dyestuffs, solvents are used such as ethanol, benzyl alcohol, propylene carbonate, dipropylene glycol. Products are found on the professional hair dressing market applying this technology.

U.S. Pat. No. 5,601,620, as well, discloses hair colouring agents with acid dyes, an organic solvent and at least one polysiloxane as a conditioner. The dyeing compositions disclosed here are having a pH in the range of 1.5-4.5.

Above two documents deal with the anionic dyes in acidic medium and they are silent on any colouring and/or lightening compositions at an alkaline pH and optionally comprising an oxidizing agent.

In an earlier European Patent application from our company with the application number 04 001 799.8, hair colouring composition is disclosed based on only anionic acidic direct dyes at alkaline medium. In that application, the possibility of addition of cationic dyestuff is disclosed to be only at minor quantities, preferably is not advised.

EP 810 851, on contrary to the above two publications, discloses hair colouring and lightening compositions comprising a cationic direct dye and an oxidizing agent. This documents is totally silent on any composition comprising anionic dyes.

In practice, further development is obviously desired by professional hair dressing practitioners and also by end consumers in order to achieve highly brilliant and long lasting colorations. Additionally, colour resistance against washing and environmental influences is highly desirable. Furthermore, partial colourations in form of streaks has become popular and products are desired showing optimal colouring and at the same time optimal lightening performance for colourful hair appearance.

This invention starts with the above mentioned problems and discloses primarily a hair colouring and secondarily a lightening composition with excellent colouring and highlighting effects together with excellent stability against washing (shampooing) and environmental influences.

Inventors of the present invention have surprisingly been found out that hair colouring compositions on aqueous basis comprising at least one direct acting anionic dyestuff and at least one direct action cationic dyestuff show excellent colouring ability and excellently stable against washing (shampooing) and environmental influences. Additionally, colouring compositions of the present invention are excellently suitable for lightening and colouring purposes when mixed with an oxidizing agent prior to application.

According to the invention the suitable direct acting anionic dyes are:

Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Among those, the most preferred anionic dyestuffs are Acid Red 52, DC Violet 2, DC Red 33, DC Orange 4, DC Red 27 and DC Yellow 10.

According to the invention, suitable cationic dyestuffs are in principal those available on the market for cosmetic hair colouring applications. For this purpose, special reference is made to the PCT application WO 95/15144 of Ciba-Geigy AG.

The cationic dyestuffs with the following chemical structure are especially, the most preferred one according to the present invention.

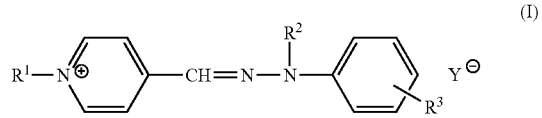

wherein $R^1$ and $R^2$ stand for hydrogen, a $CH_3$— or $C_2H_5$— group, $R^3$ stands for hydrogen, —$OCH_3$ or —$OC_2H_5$ and Y is an anion such as chloride, bromide, methosulfate.

The most preferred compound is the one according to the formula I, where $R_1$ and $R_2$, are methyl, $R_3$ is hydrogen and Y is methosulfate.

Additionally other cationic dyestuffs can as well be used in addition to the cationic dyestuffs mentioned above. Some examples to those are:
Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14 and Basic Yellow 57.

According to the invention, coloring composition comprises anionic dyes at a concentration of 0.1 to 7.5%, preferably 0.2 to 5%, more preferably 0.2 to 3% by weight calculated to total composition. Cationic dyestuffs are included into the compositions of the present invention at a concentration of 0.01 to 2.5%, preferably 0.05 to 2% and more preferably 0.05 to 1% by weight calculated to total composition.

Interestingly it has as well been found out that the ratio of acidic dyes to cationic dyes plays an important role for achieving especially resistance to washing and environmental effects. Accordingly, the ratio of cationic dyestuffs to acidic dyestuffs by weight is in the range of 3:1 to 1:10, preferably 2:1 to 1:7 and further more preferably 2:1 to 1:5.

Additionally, the coloring compositions of the present invention may comprise neutral dyes (HC dyes), so called nitro dyes for shading purposes. Concentration of those can typically be in the range from 0.01 to 2.5%, preferably 0.1 to 2% by weight calculated to total composition.

Some examples to those are: HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 1, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 1, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder, etc.

pH of the coloring compositions of the present invention varies between 5 and 12, preferably 6-11, more preferably 6.8 to 10. In the case that, the composition is used for highlighting (lightening) and coloring, the forgoing pH values refer to the pH of the dyeing composition before mixing with oxidizing agent. pH of the colouring composition is adjusted to the required pH by using triethanolamine, ammonia or its salts with acids such as ammonium chloride, ammonium sulphate, ammonium carbonate, ammonium bicarbonate, ammonium nitrate, or using alkaline solutions such as sodium hydroxide, potassium hydroxide and their respective salts with the known acids.

Colouring composition of present invention can comprise additionally in the base formulation fatty acids with 0 to 3 ethylenic bonds and with fatty acyl chain length of 12 to 22 C atom. Concentration of the fatty acids can be in the range of 0.1 to 10%, preferably 0.1 to 7.5% and most preferably 0.2 to 5% by weight calculated to the total composition. Fatty acid examples, without limiting the choice, suitable for colouring compositions are myristic acid, palmitic acid, behenic acid, steraic acid, oleic acid, linoleic acid. The most preferred fatty acid is oleic acid.

Colouring compositions according to the present invention can be in the form of emulsion, solution, dispersion and/or gel. Emulsion form is preferred.

In the case that the colouring composition is in the form of an emulsion, it comprises as an emulsion base at least one fatty alcohol or mixture of fatty alcohols with the chain length of 14 to 22 C atoms. Examples to suitable fatty alcohols, without limiting the choice, are myristyl alcohol, cetyl alcohol, stearyl alcohol, behenyl alcohol and cetostearyl alcohol. The most preferred is cetostearyl alcohol well known with its trade name Lanette O or as Lanette N in mixture with sodium cetearyl sulfate from Cognis.

The concentration of fatty alcohol(s) is in the range from 0.5 to 20%, preferably 0.5 to 15% by weight, calculated to total composition.

Colouring compositions according to present invention comprises surfactants selected from anionic, nonionic, amphoteric (or zwitterionic) and/or cationic surfactants as emulsifier or solubilizer. Cationic surfactants are as well used as hair conditioners in the colouring composition.

Anionic surfactants suitable within the scope of the invention are in principal known from the cleansing compositions and are preferably present in an amount from 0.1 to about 10%, preferably 0.2 to 7.5% and most preferably 0.2-5% by weight, calculated to the total composition.

These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula $$R_5\text{---}(C_2H_4O)_n\text{---}O\text{---}CH_2COOX,$$

wherein $R_5$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

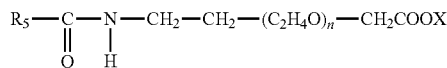

wherein $R_5$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants in a mixture.

An overview of the anionic surfactants suitable for the present invention can furthermore be found in the monography of K. Schrader, "Grundlagen und Rezepturen der Kosmetika", $2^{nd}$ Ed. (1989, Hüthig Buchverlag), pp. 595-600 and pp. 683 to 691.

Further surfactants in the colouring compositions according to the invention are nonionic surfactants alone or in admixture with anionic surfactants at a weight ratio of 3:1 to 1:3.

These are described as well in Schrader, l. c., on pages 600-601 and pp. 694-695.

Especially suited nonionic surfactants are, for example, long-chain fatty acid mono- and dialkanolamides, such as coco fatty acid mono- or diethanolamide and myristic fatty acid mono or diethanolamide, stearic acid mono or diethanolamide.

Further nonionic surfactants suited are alkyl polyglucosides of the general formula $$R_6\text{---}O\text{---}(R_3O)_n\text{---}Z_x,$$

wherein $R_6$ is an alkyl group with 8 to 18 carbon atoms, $R_3$ is an ethylene or propylene group, Z is a saccharide group with 5 to 6 carbon atoms, n is a number from 0 to 10 and x is a number between 1 and 5.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are amineoxides. Such amineoxides are state of the art, for example $C_{12}$-$C_{18}$-alkyl dimethyl amineoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl)amineoxides, or also amineoxides with ethyleneoxide and/or propyleneoxide groups in the alkyl chain. Such aminoxides are on the market, for example, under the trade names "Ammonyx®", "Aromox®" or "Genaminox®".

Further nonionic surfactants useful in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

As further surfactant component, the colouring compositions according to the invention can also contain amphoteric or zwitterionic surfactants, for example in an amount from about 0.5% to about 5%, preferably from about 1% to about 2.5% by weight, calculated to the total composition.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

In detail, it is possible to use betaines of the structures

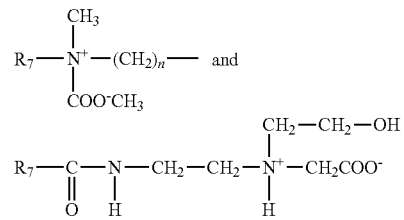

wherein $R_7$ is a $C_8$-$C_{18}$-alkyl group and n is 1 to 3; sulfobetaines of the structure

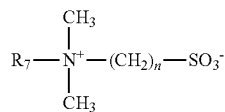

wherein $R_7$ and n are same as above; and amidoalkyl betaines of the structure

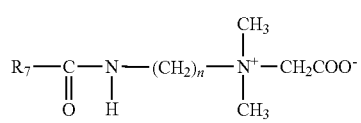

wherein $R_7$ and n are same as above.

Colouring composition can contain cationic surfactants as emulsifier, solubilizer and/or conditioning ingredients according to the formula, but not limited to.

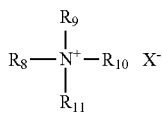

where $R_8$ is a saturated or unsaturated, branched or non-branched alkyl chain with 8-22 C atoms or

where $R_{12}$ is saturated or unsaturated, branched or non-branched alkyl chain with 7-21 C atoms and n has typical value of 1-4 or

where $R_{13}$ is saturated or unsaturated, branched or non-branched alkyl chain with 7-21 C atoms and n has typical value of 1-4, and $R_9$ is H or unsaturated or saturated, branched or non-branched alkyl chain with 1-22 C atoms or

or

where $R_{12}$, $R_{13}$ and n are same as above.

$R_{10}$ and $R_{11}$ are H or lower alkyl chain with 1 to 4 Carbon atoms, and X is typically chloride, bromide, methosulfate.

Typical examples of those ingredients are cetyl trimethly ammonium chloride, stear trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

Colouring composition can also contain cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46. Among those the most preferred one is the Polyquaternium 11 as well known with its trade name Gafquat from ISP and as Luviquat PQ from BASF.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

Typical concentration range for any of the cationic conditioners mentioned above can be 0.01-5% by weight, preferably 0.03-2.5% by weight and more preferably 0.05-1.5% by weight.

Hair dyeing composition of the present invention preferably comprise an organopolysiloxane wherein at least one silicium atom is linked to an alkylene group having a hetero-atom, in particular a nitrogen atom, with a poly-(N-acyl alkyleneimine) units of the formula

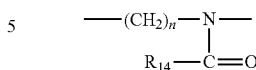

wherein n is a number from 1 to 5 and $R_{14}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

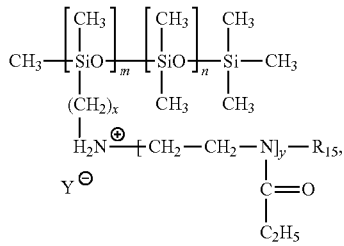

wherein m and n each are numbers from 20 to 10,000, in particular 50 to 7,000, especially 100 to 5,000, x is a number between 1 and 5, preferably 3, and y is a number from 5 to 30, $R_{15}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Colouring compositions according to the present invention can contain organic solvents as penetration enhancers and also as a solubilzers. Examples of such organic solvents are benzyloxy ethanol, benzyl alcohol, phenoxy ethanol, phenoxy isopropanol, methyl phenoxy ethanol, benzyl glycerol, N-benzyl formide, N-methylpyrrolidone, N-ethyl pyrrolidone, cinnamyl alcohol, phenethyl alcohol, p-methyl benzyl alcohol, butyl cellosolve, methyl carbitol, ethyl carbitol, propyl carbitol, butyl carbitol, diethyleneglycol, diethyl ether and dipropyleneglycol diethyl ether. Typically the concentration of those solvents can be in the range from 0.5% to 10%, preferably 0.5-5% by weight calculated to the total composition.

The hair dyeing compositions according to the invention preferably contain thickening agents. These are, for example, the various cellulose derivatives such as hydroxyalkyl celluloses, e.g. hydroxyethyl cellulose, hydroxypropyl cellulose, hydroxypropyl methyl cellulose, natural polysaccharides such as xanthan gum; guar gum and the alkoxylation products thereof in amounts from 0.1-5%, preferably 0.1-3% and most preferably 0.1-2% by weight calculated to the total composition and depending on the desired consistency thereof.

Optionally, the colouring composition of this invention can comprise further hair conditioning agents such as silicone oils either volatile or non-volatile, natural and synthetic oils. Among silicone oils those can be added to the colouring composition include dimethicone, dimethiconol, polydimethylsiloxane, DC fluid ranges from Dow Corning, natural oils such as olive oil, almond oil, avocado oil, weizenkeim oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate.

Additional non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula X or XI, respectively,

formula X

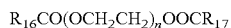
formula XI where $R_{16}$ and $R_{17}$ are independent from each other saturated, unsaturated or branched or non-branched alkyl chain with 7 to 21 C atoms and n is typically 2-100.

Another preferred compound in the colouring composition is of ceramide type of compounds according to general formula

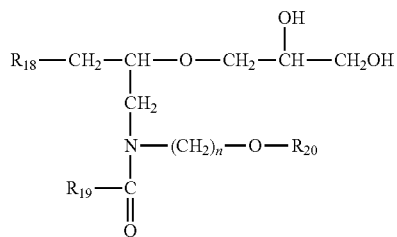

where $R_{18}$ and $R_{19}$ are independent from each other alkyl- or. alkenyl group mit 10 to 22 carbon atoms, $R_{20}$ is methyl, ethyl, n-propyl or isopropyl group and n is a number between 1 to 6, preferably 2 or 3. The concentration of ceramide type of compound in colouring compositions of the present invention can be in the range of 0.01 to 2 and especially 0.01 to 1% by weight calculated to the total composition.

Colouring composition may as well contain UV filters of oil soluble, non-ionic, ones and/or as well those of water soluble and mainly of anionic character. Examples are Benzophenone-1 Benzophenone-2, Benzophenone-3, Benzophenone-7, Benzophenone-6, Benzophenone-8, octylmethoxy cinnamate, homosalat to those of oil soluble ones and Benzophenone-4, benzophenone-9 to those anionic water soluble ones. It should be noted that the other UV filters of oil and water soluble ones should as well be possible to combine.

Another preferred way of carrying out the present invention is that mixing colouring compositions with a composition comprising at least one oxidizing agent prior to application onto hair. By doing so, lightening (highlighting) and colouring is achieved at the same time. In another words, original hair colours is lightened and at the same time dyes, stable in the presence of oxidizing agent, are deposited onto hair so that new colour appearance is achieved. The oxidizing agents suitable are hydrogen peroxide, urea peroxide, melamin peroxide or perborate salts. The most preferred is hydrogen peroxide, which is used as a lotion containing 3 to 12% by weight, calculated to composition only comprising hydrogen peroxide.

The new composition as a result of mixing colouring and oxidizing composition allows achieving simultaneous lightening and colorations. The mixing ratio of the colouring composition and oxidizing composition should be in the range of 4:1 to 1:4, by weight, preferably 2:1 to 1:3 by weight.

Colouring and highlighting with compositions of the present invention can be carried out in different ways of processing.

One of the processes is that colouring composition is mixed with an oxidizing composition and applied onto hair and after a processing time, depending on the wished lightening and as well colour tone, processed for 5 to 45 min and rinsed off from hair.

Another way of carrying out highlighting and colouring is that of two step application. In the first step, composition comprising at least one oxidizing agent is applied onto hair and left on the hair for 5 to 45 min and without rinsing off, the colouring agent is applied onto hair as a second step and after leaving onto hair additional 5 to 45 min the mixed compositions are rinsed of from hair.

In the above mentioned two step colouring and highlighting process, between the application of first and second agents, the hair can be washed with water and optionally hair can be dried.

In the lightening and colouring process using the colouring composition of the present invention, the lightening can as well be carried out with the composition known as bleaching agents. For such a process suitable bleaching composition is for example the one disclosed in a European Patent No 560 088. Preferred way of carrying out lightening an colouring using bleaching agents is two step process as mentioned above.

Another way of carrying out the invention is that addition of oxidation dyestuffs precursors (developing substances) and coupling substances into the colouring compositions of the present invention. Those oxidative dyes can as well be mixed into the colouring composition prior to application onto hair. It is possible to incorporate developing substances known per se. In the case of oxidation dyes are present in the compositions, colouring is than carried out in the presence of oxidizing agent, i.e. oxidative dye containing colouring composition is mixed with oxidizing agent prior to application. Special mention is made of p-phenylenediamine, p-methylaminophenol and substituted p-phenylenediamines such as 2,5-diamino-toluene, 2-n-propyl or 2-ethyl-p-phenylenediamine, 2,6-di-methyl-p-phenylene-diamine, 2-(2,5-diaminophenyl)ethanol, 1-amino-4-bis-(2'-hydroxy-ethyl)aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetramino pyrimidines, triaminohydroxy pyrimidines, diaminomono- and -dihydroxy pyrimidines, aminotriazines, 5-amino salicylic acid and/or 1,2,4-triamino benzene or the water-soluble salts thereof.

Further suitable aminopyridines are 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethylpyridine, 2-amino-3-hydroxypyridine, 3-amino-2 (β-hydroxyethyl amino)-6-methoxy-pyridine, 2,6-dimethyl amino-5-aminopyridine, 2-di(hydroxyethyl)amino-5-aminopyridine, 2-hydroxyethyl amino-5-aminopyridine, 4-hydroxy-2,5,6-triaminopyrimidine and/or the water-soluble salts thereof.

The total concentration of the developing substances customarily ranges between about 0.05% and 5%, preferably 0.1% and 4%, in particular 0.1% to 3% by weight, calculated to the total hair dyeing composition (excluding the oxidation agent), whereby these figures are always related to the proportion of free base.

The composition according to the present invention can contain coupling substances, which can be selected from 5-amino-2-methylphenol, 2-methyl-5-hydroxyethylaminophenol, 2,4-diaminophenoxyethanol, 2-amino-4-hydroxyethylaminoanisol, 2-methyl-5-amino-6-chlorophenol, 1,3-bis(2,4-diaminophenoxy)propane, 2-bis(2-hydroxyethyl) aminotoluene, 2-amino-5-methylphenol, resorcinol, 2-methyl resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 1,3-diaminobenzene, 1-amino-3-(2'-hydroxyethylamino)benzene, 1-amino-3-[bis(2'-hydroxy-ethyl)amino]benzene, α-naphthol, 4,6-dichlororesorcinol, 1,3-diamino-toluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof.

Further, Indole and indoline derivatives can as well be contained in the colouring composition of the present invention. Examples to those are: 6-aminoindol, 6-hydroxyindole, 1-ethyl-6-hydroxyindole, 1-methyl-4-hydroxyindol, 1-methyl-6-hydroxyindol, 2-methyl-6-hydroxyindole, 5-hydroxyindol, 4-hydroxyindol, 5,6-dihydroxyindole, 6-aminoindoline, 6-hydroxyindoline, 1-ethyl-6-hydroxyindoline, 1-methyl-4-hydroxyindoline, 1-methyl-6-hydroxyindoline, 2-methyl-6-hydroxyindoline, 5-hydroxyindoline, 4-hydroxyindoline, 5,6-dihydroxyindoline and their respective salts.

In the hair dyeing compositions according to the invention, the coupling substance(s) as reaction partners of the developing substance(s) are present in approximately the same molecular proportions as the developing substances, i.e. in amounts from 0.01% to 5.0%, preferably 0.05% to 4%, in particular 0.1% to 3% by weight, calculated to the total composition (excluding the oxidizing agent), whereby these figures are always related to the proportion of free base.

The composition of the present invention can contain additional ingredients such as preservatives, chelating agents, fragrance and substances customarily used in cosmetic colouring compositions.

The viscosity of the compositions according to the invention preferably ranges from 1,000 to 50,000, in particular 1,000 to 30,000, especially 1,000 to 20,000 mPa·s, measured at 20° C. with a Brookfield rotation viscosimeter, with spindle 5 at 5 rpm.

The invention is illustrated with the following examples, but not limited to.

| Base formulations | | |
|---|---|---|
| | % by weight I | % by weight II |
| Stearamide MEA | — | 1.50 |
| Cocamide MEA | 4.00 | 2.00 |
| Cetearyl alcohol | 10.00 | 8.00 |
| Tegin P | 1.40 | 1.40 |
| Propylene Glycol | 2.40 | 1.60 |
| Oleic acid | 3.00 | 3.00 |
| Ammonium chloride | 0.50 | 0.50 |
| Tetrasodium EDTA | 0.20 | 0.20 |
| Sodium lauryl sulfate | 1.50 | — |
| Sodium cetearyl sulfate | — | 1.20 |
| Organopolysiloxane A1 of EP 640 643 | 0.20 | 0.20 |
| Ceramide according to formula wherein $R_{18}$ and $R_{19}$ are C16 and $R_{20}$ is ethyl | — | 0.20 |
| Water | to 100 | to 100 |

The dyestuffs given in the following as for various color directions are added to the base compositions either I or II. Water amount is reduced in the base formula corresponding to the amount of dyes present in the formulations.

Dyestuff Composition Examples:

TABLE I

| | % by weight | | |
|---|---|---|---|
| | Yellow | Shiny orange red | Orange |
| Acid Red 52 | — | 1.50 | — |
| DC Yellow 10 | 1.50 | — | — |
| DC Red 33 | — | — | — |
| DC Orange 4 | — | — | 1.50 |
| Dyestuff of formula I $R_1 = R_2$ = methyl and $R_3$ = H and Y is methosulfate | 0.50 | 0.50 | 0.50 |
| Base formula | I or II | I or II | I or II |

TABLE II

| | % by weight Orange (reddish) |
|---|---|
| Acid Red 52 | — |
| DC Yellow 10 | — |
| DC Red 33 | 1.50 |
| DC Orange 4 | — |
| Dyestuff of formula I $R_1 = R_2$ = methyl and $R_3$ = H and Y is methosulfate | 0.50 |
| Base formula | I or II |

The coloring compositions so obtained show excellent dyeing performance when applied as they are without pre-mixing with any other composition.

In addition, the coloring compositions are mixed with a solution comprising 12% by weight hydrogen peroxide at a ratio of 1:2 (coloring mass:peroxide solution) and applied onto hair, in all cases, excellent highlighting and colouring effects are observed.

In order show color fastness against washing, an intensive yellow colored hair tress with a composition comprising D&C Yellow 10 and cationic yellow dye according to formula I with $R_1$=$R_2$=methyl and $R_3$=H and Y is methosulfate as presented above, was washed 10 times under usual hair wash conditions with a commercial shampoo composition designed for colored hair of the trade mark Goldwell Definition, and color of the tresses (L, a and b values) were measured before and after shampooing optically with a laboratory equipment and color differences were calculated with the well known equation to obtain ΔE values and color intensity differences (ΔL) were obtained from measured L values. The results are presented in Table III below. The test was as well carried out with compositions comprising only the cationic dyestuff of formula I with $R_1=R_2=$methyl and $R_3=$H and Y is methosulfate, at a concentration as incorporated into the inventive coloring composition and at a concentration equal to the total dyestuff content of the inventive composition (sum of concentrations anionic and cationic dyestuffs).

TABLE III

Results of durability test against wash - shampooing

|  | ΔE | ΔL |
|---|---|---|
| Inventive composition 0.5% cationic and 1.5% anionic dyestuffs | 3.7 | 3.5 |
| Comparative composition with 0.5% cationic dye | 11.7 | 0.9 |
| Comparative composition with 2% cationic dye | 4.6 | 2.2 |

The results in the table should be understood as the lower the value, the better the colourfastness against washing. Thus, the most stable color is obtained with the inventive composition.

The present invention concerns a composition for the dyeing keratin fibers especially human hair on the basis of an oxidation dyestuff precursor system reacting with peroxide and comprising additionally cationic and anionic direct dyes which provides long-lasting, intensive colors either used as such, or which can be used to obtain further shades in combination with additional developing and/or coupling agents.

The developing substances still most frequently used in hair dyeing compositions are 1,4-diaminobenzene (p-phenylenediamine) and 1-methyl-2,5-diaminobenzene (p-toluylenediamine). Although incorporation of these substances largely fulfills the user's color wishes, there are still shades that cannot be completely achieved by the use thereof or which can be intensified. Usually direct dyes of cationic and/or neutral character are used for obtaining further shades. For example, EP 850 636, EP 850 637 and EP 852 135 disclose composition based on oxidative dye precursors and cationic direct dyes. However the colors so obtained are not long last as the cationic dyes are easily washed out by subsequent shampooing and other environmental influences.

The invention therefore starts from the problem of creating a hair dyeing composition suited for the preparation of a large number of shades with especially intensive, glossy appearance and being excellently durable.

This problem is solved when such a hair dyeing composition comprises a—at least one oxidation dyestuff precursor reacting with peroxide, which is selected from pyrazole or the water-soluble salts thereof, b—at least one acidic direct dye, and c—at least one cationic direct dye selected from the compounds presented with the general formulas III, IV, V and VI

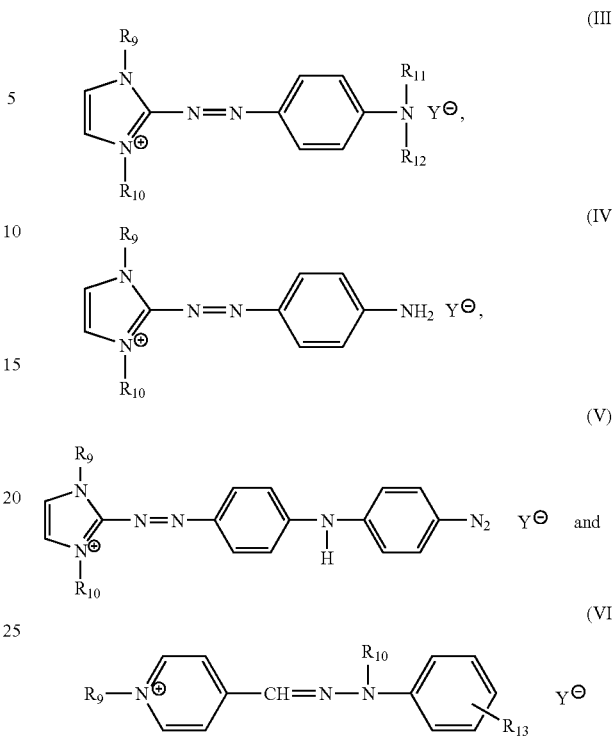

wherein $R_9$, $R_{10}$, $R_{11}$ and $R_{12}$ stand for hydrogen, a $CH_3$— or $C_2H_5$— group, $R_{13}$ stands for hydrogen, —$OCH_3$ or —$OC_2H_5$ and Y is an anion such as chloride, bromide, methosulfate.

Suitable pyrazole derivatives are such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 1-methyl-4,5-diaminopyrazole, 1-methylethyl-4,5-diaminopyrazole, 1-phenylmethyl-4,5-diaminopyrazole, 1-methyl-4,5-diaminopyrazole, 1-(4-methylphenyl)methyl-4,5-diaminopyrazole, 1-methyl-3-phenyl-4,5-diaminopyrazole and the water-soluble salts.

According to the invention the suitable direct acting anionic dyes are:
Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Among those, the most preferred anionic dyestuffs are Acid Red 52, DC Violet 2, DC Red 33, DC Orange 4, DC Red 27 and DC Yellow 10.

According to the invention, suitable cationic dyestuffs are in principal those available on the market for cosmetic hair colouring applications. For this purpose, special reference is made to the PCT application WO 95/15144 of Ciba-Geigy AG.

The most preferred cationic dyes in the colouring compositions of the present invention are the ones according to the formula III, where $R_9$, $R_{10}$, $R_{11}$ and $R_{12}$ are methyl and Y is chloride, according to formula IV where $R_9$, and $R_{10}$ are methyl and Y is chloride and according to the formula VI, where $R_9$ and $R_{10}$ are methyl, $R_{13}$ is hydrogen and Y is methosulfate.

The total concentration of the oxidation dyestuff precursors pyrazol derivatives and/or their water soluble salts customarily ranges between about 0.05% and 5%, preferably 0.1% and 4%, in particular 0.1% to 3% by weight, calculated to the total hair dyeing composition (excluding the oxidation agent), whereby these figures are always related to the proportion of free base.

According to the invention, coloring composition comprises anionic dyes at a concentration of 0.1 to 7.5%, preferably 0.2 to 5%, more preferably 0.2 to 3% by weight calculated to total composition. Cationic dyestuffs are included into the compositions of the present invention at a concentration of 0.01 to 2.5%, preferably 0.05 to 2% and more preferably 0.05 to 1.5% by weight calculated to total composition.

Interestingly it has been found out that the ratio of acidic dyes to cationic dyes plays an important role for achieving especially resistance to washing and environmental effects. Accordingly, the ratio of cationic dyestuffs to acidic dyestuffs by weight is in the range of 3:1 to 1:10, preferably 2:1 to 1:7 and further more preferably 2:1 to 1:5.

The composition according to the invention preferably comprises at least one coupling substance, which can be selected from resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2.6-dihydroxy-3,5-dimethoxypyridine, 5-amino-3-methylphenol, 6-amino-3-methylphenol, 3-amino-2-methylamino-6-methoxypyridine, 2-amino-3-hydroxy-pyridine, 2-dimethyl-amino-5-aminopyridine, 2,6-diaminopyridine, 1,3-diamino-benzene, 1-amino-3-(2'-hydroxyethylamino)benzene, 1-amino-3-[bis (2'-hydroxy-ethyl)amino]benzene, α-naphthol, 4,6-dichlororesorcinol, 1,3-diamino-toluene, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1.2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof.

However, this shall not exclude the addition of further developing and coupling substances.

The weight proportion of the named developing substances to the additional developing and coupling substances ranges between about 1:8 to 8:1, preferably about 1:5 to 5:1, in particular 1:2 to 2:1. In the hair dyeing compositions according to the invention, the coupling substance(s) as reaction partners of the developing substance(s) are present in approximately the same molecular proportions as the developing substances, i.e. in amounts from 0.01% to 5.0%, preferably 0.05% to 4%, in particular 0.1% to 3% by weight, calculated to the total composition (excluding the oxidizing agent), whereby these figures are always related to the proportion of free base.

After oxidation with peroxide, use of these compositions on the basis of a customary carrier provides very expressive, intensive, long-lasting hair colorations, which can be varied to achieve further shades by the addition of the respective further developing and coupling substances.

It is also possible to incorporate additional developing substances known per se. Suitable are tetraminopyrimidines are in particular 2,4,5,6-tetraminopyrimidine and the lower alkyl derivatives thereof; suitable triaminohydroxypyrimidines are, for example 4-hydroxy-2,5,6-triaminopyrimidine, 2-hydroxy-4,5,6-triaminopyrimidine and 5-hydroxy-2,4,6-triaminopyrimidine; suitable mono- and diamino dihydroxypyrimidines are, for example, 2,6-dihydroxy-4,5-diaminopyrimidine, 2,4-diamino-6-hydroxy-pyrimidine or 4,6-dihydroxy-2,5-diaminopyrimidine or the water-soluble salts thereof, aminophenol derivatives such as 4-aminophenol, 4-amino-3-methylphenol, 2-chloro-4-aminophenol, 2,6-dichloro-4-aminophenol, 2,4-diamino-phenol, 2,6-dibromo-4-aminophenol and/or 2-aminophenol and water-soluble salts thereof, furthermore, phenylenedimanine derivatives such as 2,5-diamino-toluene, 2-n-propyl or 2-ethyl-p-phenylene-diamine, 2,6-dimethyl-p-phenylenediamine, 2-(2,5-diaminophenyl)ethanol, 1-amino-4-bis-(2'-hydroxy-ethyl) aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1.3-dimethyl-2,5-diaminobenzene, 1.4-diamino isopropyl benzene and/or 1-amino-4-β-hydroxypropyl aminobenzene or the water-soluble salts thereof.

Additionally other cationic dyestuffs can as well be used in addition to the cationic dyestuffs mentioned above. Some examples to those are:
Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14 and Basic Yellow 57.

Additionally, the coloring compositions of the present invention may comprise neutral dyes (HC dyes), so called nitro dyes for shading purposes. Concentration of those can typically be in the range from 0.01 to 2.5%, preferably 0.1 to 2% by weight calculated to total composition.

Some examples to those are: HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 1, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 1, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder, etc.

Hair dyeing composition of the present invention preferably comprise an organopolysiloxane wherein at least one silicium atom is linked to an alkylene group having a heteroatom, in particular a nitrogen atom, with a poly-(N-acyl alkyleneimine) units of the formula

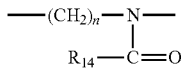

wherein n is a number from 1 to 5 and $R_{14}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

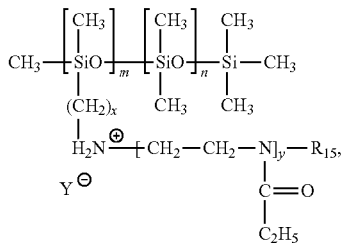

wherein m and n each are numbers from 20 to 10,000, in particular 50 to 7,000, especially 100 to 5,000, x is a number between 1 and 5, preferably 3, and y is a number from 5 to 30, $R_{15}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Another preferred compound in the colouring composition is of ceramide type of compounds according to general formula

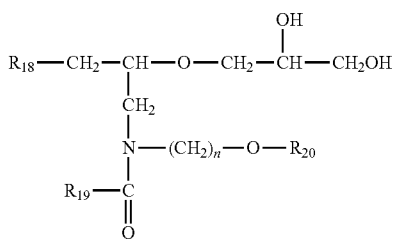

where $R_{18}$ and $R_{19}$ are independent from each other alkyl- or. alkenyl group mit 10 to 22 carbon atoms, $R_{20}$ is methyl, ethyl, n-propyl or isopropyl group and n is a number between 1 to 6, preferably 2 or 3. The concentration of ceramide type of compound in colouring compositions of the present invention can be in the range of 0.01 to 2 and especially 0.01 to 1% by weight calculated to the total composition.

The compositions of the present invention can comprise one or more ubiquinone of the formula.

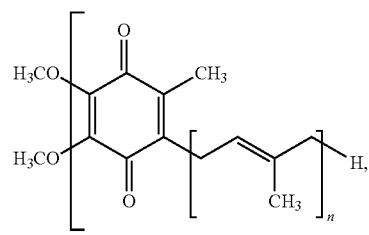

wherein n is a number from 1 to 10. Concentration of ubichinones in the compositions of the present invention can vary between 0.001% and 10% by weight, calculated to the total composition excluding oxidizing agent.

Coloring composition of the present invention can certainly comprise compounds for accelerating (catalysts) the oxidative dyeing keratin fibres such as iodine salts i.e. potassium or sodium iodide and/or dihydroxy acetone.

The hair dyeing compositions according to the invention can comprise the basic substances and additives customarily found in such compositions, conditioning agents, etc., known as state of the art and described, for example, in the monography of K. Schrader, "Grundlagen und Rezepturen der Kosmetika", 2nd Ed. (Hüthig Buch Verlag, Heidelberg, 1989), pp. 782 to 815. They can be prepared as solutions, creams, gels or also in the form of aerosol products; suitable carrier material compositions are known as state of the art.

For application, the oxidation dyestuff precursor is mixed with an oxidizing agent. The preferred oxidizing agent is hydrogen peroxide, for example in a concentration of 2 to 12% by weight. However, the use of other peroxides such as urea peroxide and melamine peroxide is also possible.

As an alternative to peroxide oxidation, it is also possible to achieve the oxidation by air, for example, by applying onto the hair a composition comprising an oxidation dyestuff precursor as aerosol foam and leaving to process for about 15 to 20 minutes.

The pH-value of the ready-to-use hair dyeing composition, i.e. after mixing with peroxide, can be between 5 and 12, preferably 6-11, more preferably 6.8 to 10.

The following examples are to illustrate the invention without limiting it.

| Carrier | |
|---|---|
| Stearyl alcohol | 8.0 (% by wt.) |
| Coco fatty acid monoethanolamide | 4.5 |
| 1.2-Propanediol mono/distearate | 1.3 |
| Coco fatty alcohol polyglycolether | 4.0 |
| Sodium lauryl sulfate | 1.0 |
| Oleic acid | 2.0 |
| 1.2-Propanediol | 1.5 |
| Na-EDTA | 0.5 |
| Sodium sulfite | 1.0 |
| Protein hydrolyzate | 0.5 |
| Ceramide according to formula where $R_{18}$ and $R_{19}$ are C16 and $R_{20}$ is ethyl | 0.2 |
| Ascorbic acid | 0.2 |
| Organopolisiloxane according to EP640643 Compound A-1 | 0.3 |
| Perfume | 0.4 |
| Ubichinone 10 | 0.1 |
| Ammonia, 25% | 1.0 |
| Ammonium chloride | 0.5 |
| Panthenol | 0.8 |
| Water | ad 100.00 |

The dyestuff combinations either oxidative or direct dyes of anionic and cationic characters were incorporated into this carrier, whereby the water content was reduced accordingly. The colorations were carried out on wool patches, strands of bleached human hair and natural human hair at a color level of 8 by application of a 1:1 mixture of an emulsion comprising the dyestuffs as given in the examples below and a 6% hydrogen peroxide solution (pH-value of the mixture: 9.8) with 30 minutes processing at room temperature, subsequent rinsing and drying.

The following colorations were obtained:

TABLE I

Examples 1 to 5

| | \multicolumn{5}{c}{Example} |
|---|---|---|---|---|---|
| | I | II | III | IV | V |
| | \multicolumn{5}{c}{(all values are weight %)} |
| 1-Hydroxyethyl-4,5-diamino-pyrazole sulfate | 1.05 | 1.05 | 1.05 | 1.05 | 1.05 |
| 4-amino-3-hydroxytoluene | 0.54 | 0.54 | 0.54 | 0.54 | 0.54 |
| $R_9 = R_{10} = R_{11} = R_{12}$ = methyl and Y is chloride | 0.06 | 0.04 | 0.02 | 0.08 | — |
| Acid red 52 | 0.02 | 0.04 | 0.06 | — | 0.08 |

Examples I to III are according to the invention and examples IV and V are for comparative purposes.

The coloring compositions so obtained show excellent dyeing performance.

In order show color fastness (durability) against washing, all colored strands were washed 10 times under usual hair wash conditions with a commercial shampoo composition designed for colored hair of the trade mark Goldwell Definition, and color of the tresses (L, a and b values) were measured before and after shampooing optically with a laboratory equipment and color differences were calculated with the well known equation to obtain ΔE values and color intensity differences (ΔL) were obtained from measured L values. The results are presented in the Table II below.

TABLE II

Results of the durability test

| Example | L1 | L2 | ΔE |
|---|---|---|---|
| I | 35.6 | 37.0 | 7.8 |
| II | 37.0 | 38.9 | 5.8 |
| III | 37.5 | 40.6 | 6.7 |
| IV | 35.3 | 40.5 | 10.5 |
| V | 36.0 | 42.0 | 11.0 |

L1 stands for the intensity of the color measured before the washing test and L2 is the same value measured after washing the strands 10 times with shampoo. ΔE value is obtained from the L, a and b values measured before and after washing. As it is obvious from the table immediately after coloring there is no real difference in the intensity though shade differences were obvious (not shown). However, after washing the strands with shampoo, intensity differences were obvious between the strands colored only with either cationic or anionic dyes (non inventive examples IV and V, respectively) and the strands colored with mixture of anionic and cationic dyes according to the present invention. This is furthermore expressed with ΔE values as the color difference.

The present invention concerns a composition for the dyeing keratin fibers especially human hair on the basis of an oxidation dyestuff precursor system reacting with peroxide and comprising additionally cationic and anionic direct dyes which provides long-lasting, intensive colors either used as such, or which can be used to obtain further shades in combination with additional developing and/or coupling agents.

The developing substances still most frequently used in hair dyeing compositions are 1,4-diaminobenzene (p-phenylenediamine) and 1-methyl-2,5-diaminobenzene (p-toluylenediamine). Although incorporation of these substances largely fulfills the user's color wishes, there are still shades that cannot be completely achieved by the use thereof or which can be intensified. Usually direct dyes of cationic and/or neutral character are used for obtaining further shades. For example, EP 850 636, EP 850 637 and EP 852 135 disclose composition based on oxidative dye precursors and cationic direct dyes. However the colors so obtained are not long last as the cationic dyes are easily washed out by subsequent shampooing and other environmental influences.

The invention therefore starts from the problem of creating a hair dyeing composition suited for the preparation of a large number of shades with especially intensive, glossy appearance and being excellently durable.

This problem is solved when such a hair dyeing composition comprises a—at least one oxidation dyestuff precursor reacting with peroxide, which is selected from tetraminopyrimidines, triaminohydroxypyrimidines, diamino mono- and -dihydroxy-pyrimidines and/or aminotriazines or water-soluble salts thereof, b—at least one acidic direct dye, and c—at least one cationic direct dye selected from the compounds presented with the general formulas III, IV, V and VI

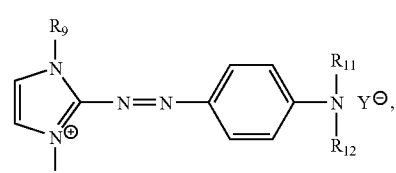

(III)

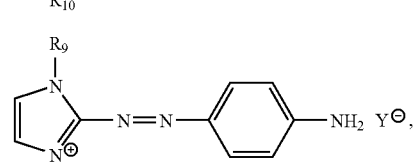

(IV)

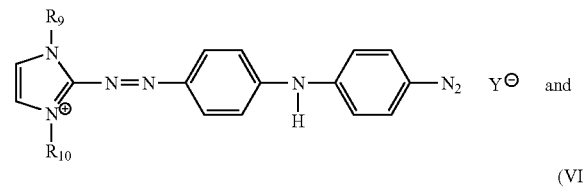

(V)

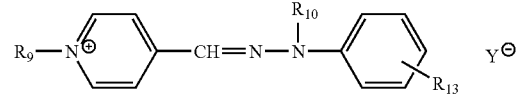

(VI)

wherein $R_9$, $R_{10}$, $R_{11}$ and $R_{12}$ stand for hydrogen, a $CH_3$— or $C_2H_5$— group, $R_{13}$ stands for hydrogen, —$OCH_3$ or —$OC_2H_5$ and Y is an anion such as chloride, bromide, methosulfate.

Suitable tetraminopyrimidines are in particular 2,4,5,6-tetraminopyrimidine and the lower alkyl derivatives thereof; suitable triaminohydroxypyrimidines are, for example 4-hydroxy-2,5,6-triaminopyrimidine, 2-hydroxy-4,5,6-triaminopyrimidine and 5-hydroxy-2,4,6-triaminopyrimidine; suitable mono- and diamino dihydroxypyrimidines are, for example, 2,6-dihydroxy-4,5-diaminopyrimidine, 2,4-diamino-6-hydroxy-pyrimidine or 4,6-dihydroxy-2,5-diaminopyrimidine or the water-soluble salts thereof; a preferred amino-substituted triazine is 2,4-diamino-1,3,5-triazine.

According to the invention the suitable direct acting anionic dyes are:
Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Among those, the most preferred anionic dyestuffs are Acid Red 52, DC Violet 2, DC Red 33, DC Orange 4, DC Red 27 and DC Yellow 10.

According to the invention, suitable cationic dyestuffs are in principal those available on the market for cosmetic hair colouring applications. For this purpose, special reference is made to the PCT application WO 95/15144 of Ciba-Geigy AG.

The most preferred cationic dyes in the colouring compositions of the present invention are the ones according to the formula III, where $R_9$, $R_{10}$, $R_{11}$ and $R_{12}$ are methyl and Y is chloride, according to formula IV where $R_9$, and $R_{10}$ are methyl and Y is chloride and according to the formula VI, where $R_9$ and $R_{10}$ are methyl, $R_{13}$ is hydrogen and Y is methosulfate.

The total concentration of the oxidation dyestuff precursors aminopyrimidine derivatives and/or their water soluble salts customarily ranges between about 0.05% and 5%, preferably 0.1% and 4%, in particular 0.1% to 3% by weight, calculated to the total hair dyeing composition (excluding the oxidation agent), whereby these figures are always related to the proportion of free base.

According to the invention, coloring composition comprises anionic dyes at a concentration of 0.1 to 7.5%, preferably 0.2 to 5%, more preferably 0.2 to 3% by weight calculated to total composition. Cationic dyestuffs are included into the compositions of the present invention at a concentration of 0.01 to 2.5%, preferably 0.05 to 2% and more preferably 0.05 to 1.5% by weight calculated to total composition.

Interestingly it has been found out that the ratio of acidic dyes to cationic dyes plays an important role for achieving especially resistance to washing and environmental effects. Accordingly, the ratio of cationic dyestuffs to acidic dyestuffs by weight is in the range of 3:1 to 1:10, preferably 2:1 to 1:7 and further more preferably 2:1 to 1:5.

The composition according to the invention preferably comprises at least one coupling substance, which can be selected from resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2.6-dihydroxy-3,5-dimethoxypyridine, 5-amino-3-methylphenol, 6-amino-3-methylphenol, 3-amino-2-methylamino-6-methoxypyridine, 2-amino-3-hydroxy-pyridine, 2-dimethyl-amino-5-aminopyridine, 2,6-diaminopyridine, 1,3-diamino-benzene, 1-amino-3-(2'-hydroxyethylamino)benzene, 1-amino-3-[bis(2'-hydroxy-ethyl)amino]benzene, α-naphthol, 4,6-dichlororesorcinol, 1,3-diamino-toluene, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1.2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof.

However, this shall not exclude the addition of further developing and coupling substances.

The weight proportion of the named developing substances to the additional developing and coupling substances ranges between about 1:8 to 8:1, preferably about 1:5 to 5:1, in particular 1:2 to 2:1. In the hair dyeing compositions according to the invention, the coupling substance(s) as reaction partners of the developing substance(s) are present in approximately the same molecular proportions as the developing substances, i.e. in amounts from 0.01% to 5.0%, preferably 0.05% to 4%, in particular 0.1% to 3% by weight, calculated to the total composition (excluding the oxidizing agent), whereby these figures are always related to the proportion of free base.

After oxidation with peroxide, use of these compositions on the basis of a customary carrier provides very expressive, intensive, long-lasting hair colorations, which can be varied to achieve further shades by the addition of the respective further developing and coupling substances.

It is also possible to incorporate additional developing substances known per se. pyrazole or triazole derivatives such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 5-amino-salicylic acid and/or 1,2,4-triaminobenzene and the water-soluble salts thereof, aminophenol derivatives such as 4-aminophenol, 4-amino-3-methylphenol, 2-chloro-4-aminophenol, 2,6-dichloro-4-aminophenol, 2,4-diamino-phenol, 2,6-dibromo-4-aminophenol and/or 2-aminophenol and water-soluble salts thereof, furthermore, phenylenedimanine derivatives such as 2,5-diamino-toluene, 2-n-propyl or 2-ethyl-p-phenylene-diamine, 2,6-dimethyl-p-phenylenediamine, 2-(2,5-diaminophenyl)ethanol, 1-amino-4-bis-(2'-hydroxy-ethyl)aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1.3-dimethyl-2,5-diaminobenzene, 1.4-diamino isopropyl benzene and/or 1-amino-4-β-hydroxypropyl aminobenzene or the water-soluble salts thereof.

Additionally other cationic dyestuffs can as well be used in addition to the cationic dyestuffs mentioned above. Some examples to those are:

Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14 and Basic Yellow 57.

Additionally, the coloring compositions of the present invention may comprise neutral dyes (HC dyes), so called nitro dyes for shading purposes. Concentration of those can typically be in the range from 0.01 to 2.5%, preferably 0.1 to 2% by weight calculated to total composition.

Some examples to those are: HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 1, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 1, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder, etc.

Hair dyeing composition of the present invention preferably comprise an organopolysiloxane wherein at least one silicium atom is linked to an alkylene group having a heteroatom, in particular a nitrogen atom, with a poly-(N-acyl alkyleneimine) units of the formula

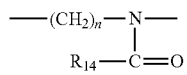

wherein n is a number from 1 to 5 and $R_{14}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

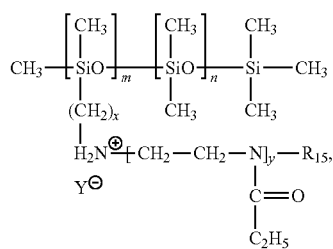

wherein m and n each are numbers from 20 to 10,000, in particular 50 to 7,000, especially 100 to 5,000, x is a number between 1 and 5, preferably 3, and y is a number from 5 to 30, $R_{15}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Another preferred compound in the colouring composition is of ceramide type of compounds according to general formula

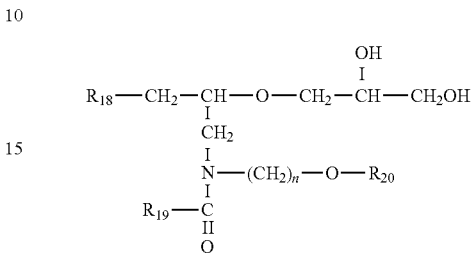

where $R_{18}$ and $R_{19}$ are independent from each other alkyl- or. alkenyl group mit 10 to 22 carbon atoms, $R_{20}$ is methyl, ethyl, n-propyl or isopropyl group and n is a number between 1 to 6, preferably 2 or 3. The concentration of ceramide type of compound in colouring compositions of the present invention can be in the range of 0.01 to 2 and especially 0.01 to 1% by weight calculated to the total composition.

The compositions of the present invention can comprise one or more ubiquinone of the formula.

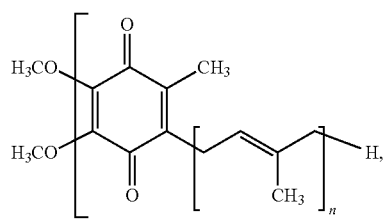

wherein n is a number from 1 to 10. Concentration of ubichinones in the compositions of the present invention can vary between 0.001% and 10% by weight, calculated to the total composition excluding oxidizing agent.

Coloring composition of the present invention can certainly comprise compounds for accelerating (catalysts) the oxidative dyeing keratin fibres such as iodine salts i.e. potassium or sodium iodide and/or dihydroxy acetone.

The hair dyeing compositions according to the invention can comprise the basic substances and additives customarily found in such compositions, conditioning agents, etc., known as state of the art and described, for example, in the monography of K. Schrader, "Grundlagen und Rezepturen der Kosmetika", 2nd Ed. (Hüthig Buch Verlag, Heidelberg, 1989), pp. 782 to 815. They can be prepared as solutions, creams, gels or also in the form of aerosol products; suitable carrier material compositions are known as state of the art.

For application, the oxidation dyestuff precursor is mixed with an oxidizing agent. The preferred oxidizing agent is hydrogen peroxide, for example in a concentration of 2 to 12% by weight. However, the use of other peroxides such as urea peroxide and melamine peroxide is also possible.

As an alternative to peroxide oxidation, it is also possible to achieve the oxidation by air, for example, by applying onto the hair a composition comprising an oxidation dyestuff precursor as aerosol foam and leaving to process for about 15 to 20 minutes.

The pH-value of the ready-to-use hair dyeing composition, i.e. after mixing with peroxide, can be between 5 and 12, preferably 6-11, more preferably 6.8 to 10.

The following examples are to illustrate the invention without limiting it.

| Carrier | |
|---|---|
| Stearyl alcohol | 8.0 (% by wt.) |
| Coco fatty acid monoethanolamide | 4.5 |
| 1.2-Propanediol mono/distearate | 1.3 |
| Coco fatty alcohol polyglycolether | 4.0 |
| Sodium lauryl sulfate | 1.0 |
| Oleic acid | 2.0 |
| 1.2-Propanediol | 1.5 |
| Na-EDTA | 0.5 |
| Sodium sulfite | 1.0 |
| Protein hydrolyzate | 0.5 |
| Ceramide according to formula where $R_{18}$ and $R_{19}$ are C16 and $R_{20}$ is ethyl | 0.2 |
| Ascorbic acid | 0.2 |
| Organopolisiloxane according to EP640643 Compound A-1 | 0.3 |
| Perfume | 0.4 |
| Ubichinone 10 | 0.1 |
| Ammonia, 25% | 1.0 |
| Ammonium chloride | 0.5 |
| Panthenol | 0.8 |
| Water | ad 100.00 |

The dyestuff combinations either oxidative or direct dyes of anionic and cationic characters were incorporated into this carrier, whereby the water content was reduced accordingly. The colorations were carried out on wool patches, strands of bleached human hair and natural human hair at a color level of 8 by application of a 1:1 mixture of an emulsion comprising the dyestuffs as given in the examples below and a 6% hydrogen peroxide solution (pH-value of the mixture: 9.8) with 30 minutes processing at room temperature, subsequent rinsing and drying.

The following colorations were obtained:

TABLE I

Examples 1 to 5

| | Example | | | | |
|---|---|---|---|---|---|
| | I | II | III | IV | V |
| | (all values are weight %) | | | | |
| 4-Hydroxy-2,5,6-triamino-pyrimidine sulfate | 1.04 | 1.04 | 1.04 | 1.04 | 1.04 |
| 2-methyl-5-hydroxyethylaminophenol | 0.73 | 0.73 | 0.73 | 0.73 | 0.73 |
| $R_9 = R_{10} = R_{11} = R_{12}$ = methyl and Y is chloride | 0.06 | 0.04 | 0.02 | 0.08 | — |
| Acid red 52 | 0.02 | 0.04 | 0.06 | — | 0.08 |

Examples I to III are according to the invention and examples IV and V are for comparative purposes.

The coloring compositions so obtained show excellent dyeing performance.

In order show color fastness (durability) against washing, all colored strands were washed 10 times under usual hair wash conditions with a commercial shampoo composition designed for colored hair of the trade mark Goldwell Definition, and color of the tresses (L, a and b values) were measured before and after shampooing optically with a laboratory equipment and color differences were calculated with the well known equation to obtain ΔE values and color intensity differences (ΔL) were obtained from measured L values. The results are presented in the Table II below.

TABLE II

Results of the durability test

| Example | L1 | L2 | ΔE |
|---|---|---|---|
| I | 31.1 | 32.8 | 7.8 |
| II | 32.6 | 33.5 | 5.2 |
| III | 33.1 | 35.2 | 4.7 |
| IV | 30.3 | 36 | 12.5 |
| V | 31.0 | 40 | 16.0 |

L1 stands for the intensity of the color measured before the washing test and L2 is the same value measured after washing the strands 10 times with shampoo. ΔE value is obtained from the L, a and b values measured before and after washing. As it is obvious from the table immediately after coloring there is no real difference in the intensity though shade differences were obvious (not shown). However, after washing the strands with shampoo, intensity differences were obvious between the strands colored only with either cationic or anionic dyes (non inventive examples IV and V, respectively) and the strands colored with mixture of anionic and cationic dyes according to the present invention. This is furthermore expressed with ΔE values as the color difference.

The present invention concerns a composition for the dyeing keratin fibers especially human hair on the basis of an oxidation dyestuff precursor system reacting with peroxide and comprising additionally cationic and anionic direct dyes which provides long-lasting, intensive colors either used as such, or which can be used to obtain further shades in combination with additional developing and/or coupling agents.

The developing substances still most frequently used in hair dyeing compositions are 1,4-diaminobenzene (p-phenylenediamine) and 1-methyl-2,5-diaminobenzene (p-toluylenediamine). Although incorporation of these substances largely fulfills the user's color wishes, there are still shades that cannot be completely achieved by the use thereof or which can be intensified. Usually direct dyes of cationic and/or neutral character are used for obtaining further shades. For example, EP 850 636, EP 850 637 and EP 852 135 disclose composition based on oxidative dye precursors and cationic direct dyes. However the colors so obtained are not long last as the cationic dyes are easily washed out by subsequent shampooing and other environmental influences.

The invention therefore starts from the problem of creating a hair dyeing composition suited for the preparation of a large number of shades with especially intensive, glossy appearance and being excellently durable.

This problem is solved when such a hair dyeing composition comprises a—at least one oxidation dyestuff precursor reacting with peroxide, which is selected from 4-aminophenol and the derivatives thereof of the general formula (I)

(I)

wherein R is a $C_1$-$C_3$-alkyl group, a hydroxy-$C_1$-$C_3$-alkyl group or a halogen atom, in particular Cl, and n is a number from 0 to 2, and/or 2-aminophenol and/or 1,4 diaminobenzene and substituted p-phenylenediamines and the derivatives thereof of the general formula II

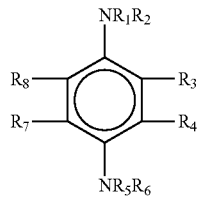

wherein $R_1$ and $R_2$ are same or different, and stands for hydrogen, $C_1$-$C_4$ alkyl, $C_1$-$C_4$ hydroxyalkyl, isopropyl, phenyl or p-aminophenyl, $R_3$ is hydrogen, $C_1$-$C_4$ alkyl, $C_1$-$C_4$ hydroxyalkyl, $C_1$-$C_4$ alkoxy, chloride or isopropyl, $R_4$ is hydrogen, halogen, in particular chloride, $C_1$-$C_4$ alkyl or $C_1$-$C_4$ hydroxyalkyl, $R_5$ and $R_6$ are the same or different, a group selected from hydrogen, C1-C4 alkyl, C1-C4 hydroxyalkyl or isopropyl, $R_7$ is hydrogen and $R_8$ is a group selected from hydrogen, hydroxyl, $C_1$-$C_4$ alkyl, $C_1$-$C_4$ hydroxyalkyl or isopropyl, b—at least one acidic direct dye, and
c—at least one cationic direct dye selected from the compounds presented with the general formulas III, IV, V and VI

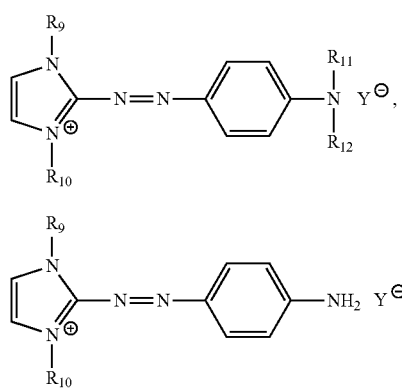

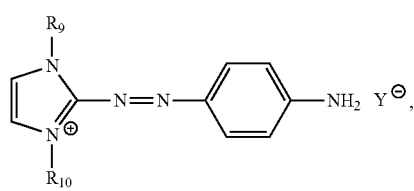

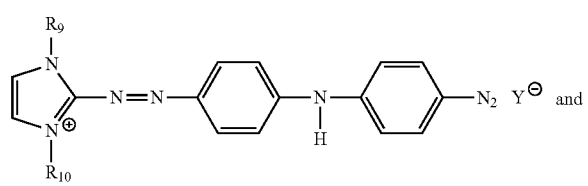

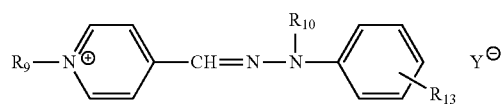

wherein $R_9$, $R_{10}$, $R_{11}$ and $R_{12}$ stand for hydrogen, a $CH_3$— or $C_2H_5$— group, $R_{13}$ stands for hydrogen, —$OCH_3$ or —$OC_2H_5$ and Y is an anion such as chloride, bromide, methosulfate.

Oxidation dyestuff precursors preferred according to formula I above are 4-aminophenol, 4-amino-3-methylphenol, 2-chloro-4-aminophenol, 2,6-dichloro-4-aminophenol, 2,4-diamino-phenol, 2,6-dibromo-4-aminophenol and/or 2-aminophenol and water-soluble salts thereof.

Oxidation dyestuff precursors preferred according to formula II above are in particular 2,5-diamino-toluene, 2-n-propyl or 2-ethyl-p-phenylene-diamine, 2,6-dimethyl-p-phenylenediamine, 2-(2,5-diaminophenyl)ethanol, 1-amino-4-bis-(2'-hydroxy-ethyl)aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1.3-dimethyl-2,5-diaminobenzene, 1.4-diamino isopropyl benzene and/or 1-amino-4-β-hydroxypropyl aminobenzene or the water-soluble salts thereof.

According to the invention the suitable direct acting anionic dyes are:
Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Among those, the most preferred anionic dyestuffs are Acid Red 52, DC Violet 2, DC Red 33, DC Orange 4, DC Red 27 and DC Yellow 10.

According to the invention, suitable cationic dyestuffs are in principal those available on the market for cosmetic hair colouring applications. For this purpose, special reference is made to the PCT application WO 95/15144 of Ciba-Geigy AG.

The most preferred cationic dyes in the colouring compositions of the present invention are the ones according to the formula III, where $R_9$, $R_{10}$, $R_{11}$ and $R_{12}$ are methyl and Y is chloride, according to formula IV where $R_9$, and $R_{10}$ are methyl and Y is chloride and according to the formula VI, where $R_9$ and $R_{10}$ are methyl, $R_{13}$ is hydrogen and Y is methosulfate.

The total concentration of the oxidation dyestuff precursors according to the formula I and/or II customarily ranges between about 0.05% and 5%, preferably 0.1% and 4%, in particular 0.1% to 3% by weight, calculated to the total hair dyeing composition (excluding the oxidation agent), whereby these figures are always related to the proportion of free base.

According to the invention, coloring composition comprises anionic dyes at a concentration of 0.1 to 7.5%, preferably 0.2 to 5%, more preferably 0.2 to 3% by weight calculated to total composition. Cationic dyestuffs are included into the compositions of the present invention at a concentration of 0.01 to 2.5%, preferably 0.05 to 2% and more preferably 0.05 to 1.5% by weight calculated to total composition.

Interestingly it has been found out that the ratio of acidic dyes to cationic dyes plays an important role for achieving especially resistance to washing and environmental effects. Accordingly, the ratio of cationic dyestuffs to acidic dyestuffs by weight is in the range of 3:1 to 1:10, preferably 2:1 to 1:7 and further more preferably 2:1 to 1:5.

The composition according to the invention preferably comprises at least one coupling substance, which can be selected from resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2.6-dihydroxy-3,5-dimethoxypyridine, 5-amino-3-methylphenol, 6-amino-3-methylphenol, 3-amino-2-methylamino-6-methoxypyridine, 2-amino-3-hydroxy-pyridine, 2-dimethyl-amino-5-aminopyridine, 2,6-diaminopyridine, 1,3-diamino-benzene, 1-amino-3-(2'-hydroxyethylamino)benzene, 1-amino-3-[bis(2'-hydroxy-ethyl)amino]benzene, α-naphthol, 4,6-dichlororesorcinol, 1,3-diamino-toluene, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1.2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof.

However, this shall not exclude the addition of further developing and coupling substances.

The weight proportion of the named developing substances to the additional developing and coupling substances ranges between about 1:8 to 8:1, preferably about 1:5 to 5:1, in particular 1:2 to 2:1. In the hair dyeing compositions according to the invention, the coupling substance(s) as reaction partners of the developing substance(s) are present in approximately the same molecular proportions as the developing substances, i.e. in amounts from 0.01% to 5.0%, preferably 0.05% to 4%, in particular 0.1% to 3% by weight, calculated to the total composition (excluding the oxidizing agent), whereby these figures are always related to the proportion of free base.

After oxidation with peroxide, use of these compositions on the basis of a customary carrier provides very expressive, intensive, long-lasting hair colorations, which can be varied to achieve further shades by the addition of the respective further developing and coupling substances.

It is also possible to incorporate additional developing substances known per se. pyrazole or triazole derivatives such as 1-hydroxyethyl-4.5-diaminopyrazole, 3.4-diamino-5-hydroxypyrazole, 3.5-diaminopyrazole, 3.5-diamino pyrazol-1-carboxamide, 3-amino-5-hydroxypyrazole, 1-phenyl-2-methylpyrazole, 1-phenyl-3-methylpyrazole-5-one, 3.5-dimethylpyrazole, 3.5-dimethylpyrazole-1-methanol, 3.5-diamino-1.2.4-triazole, tetraminopyrimidine, triaminohydroxypyrimidine, diamino mono- and dihydroxypyrimidine, aminotriazines, 5-amino-salicylic acid and/or 1.2.4-triaminobenzene and the water-soluble salts thereof.

Additionally other cationic dyestuffs can as well be used in addition to the cationic dyestuffs mentioned above. Some examples to those are:
Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14 and Basic Yellow 57.

Additionally, the coloring compositions of the present invention may comprise neutral dyes (HC dyes), so called nitro dyes for shading purposes. Concentration of those can typically be in the range from 0.01 to 2.5%, preferably 0.1 to 2% by weight calculated to total composition.

Some examples to those are: HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 1, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder, etc.

Hair dyeing composition of the present invention preferably comprise an organopolysiloxane wherein at least one silicium atom is linked to an alkylene group having a heteroatom, in particular a nitrogen atom, with a poly-(N-acyl alkyleneimine) units of the formula

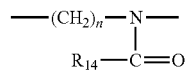

wherein n is a number from 1 to 5 and $R_{14}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

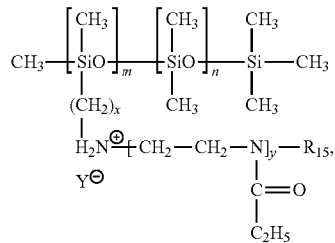

wherein m and n each are numbers from 20 to 10,000, in particular 50 to 7,000, especially 100 to 5,000, x is a number between 1 and 5, preferably 3, and y is a number from 5 to 30, $R_{15}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition. Another preferred compound in the colouring composition is of ceramide type of compounds according to general formula

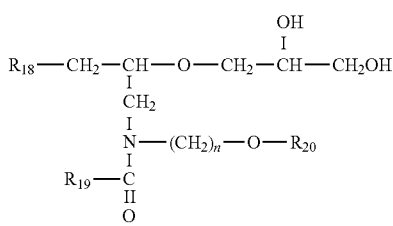

where $R_{18}$ and $R_{19}$ are independent from each other alkyl- or alkenyl group mit 10 to 22 carbon atoms, $R_{20}$ is methyl, ethyl, n-propyl or isopropyl group and n is a number between 1 to 6, preferably 2 or 3. The concentration of ceramide type of compound in colouring compositions of the present invention can be in the range of 0.01 to 2 and especially 0.01 to 1% by weight calculated to the total composition.

The compositions of the present invention can comprise one or more ubiquinone of the formula.

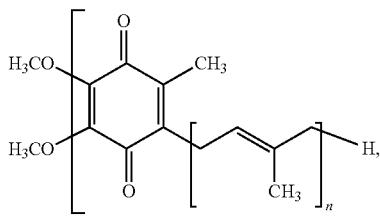

wherein n is a number from 1 to 10. Concentration of ubichinones in the compositions of the present invention can vary between 0.001% and 10% by weight, calculated to the total composition excluding oxidizing agent.

Coloring composition of the present invention can certainly comprise compounds for accelerating (catalysts) the oxidative dyeing keratin fibres such as iodine salts i.e. potassium or sodium iodide and/or dihydroxy acetone.

The hair dyeing compositions according to the invention can comprise the basic substances and additives customarily found in such compositions, conditioning agents, etc., known as state of the art and described, for example, in the monography of K. Schrader, "Grundlagen und Rezepturen der Kosmetika", 2nd Ed. (Hüthig Buch Verlag, Heidelberg, 1989), pp. 782 to 815. They can be prepared as solutions, creams, gels or also in the form of aerosol products; suitable carrier material compositions are known as state of the art.

For application, the oxidation dyestuff precursor is mixed with an oxidizing agent. The preferred oxidizing agent is hydrogen peroxide, for example in a concentration of 2 to 12% by weight. However, the use of other peroxides such as urea peroxide and melamine peroxide is also possible.

As an alternative to peroxide oxidation, it is also possible to achieve the oxidation by air, for example, by applying onto the hair a composition comprising an oxidation dyestuff precursor as aerosol foam and leaving to process for about 15 to 20 minutes.

The pH-value of the ready-to-use hair dyeing composition, i.e. after mixing with peroxide, can be between 5 and 12, preferably 6-11, more preferably 6.8 to 10.

The following examples are to illustrate the invention without limiting it.

| Carrier | |
|---|---|
| Stearyl alcohol | 8.0 (% by wt.) |
| Coco fatty acid monoethanolamide | 4.5 |
| 1.2-Propanediol mono/distearate | 1.3 |
| Coco fatty alcohol polyglycolether | 4.0 |
| Sodium lauryl sulfate | 1.0 |
| Oleic acid | 2.0 |
| 1.2-Propanediol | 1.5 |
| Na-EDTA | 0.5 |
| Sodium sulfite | 1.0 |
| Protein hydrolyzate | 0.5 |
| Ceramide according to formula where $R_{18}$ and $R_{19}$ are C16 and $R_{20}$ is ethyl | 0.2 |
| Ascorbic acid | 0.2 |
| Organopolisiloxane according to EP640643 Compound A-1 | 0.3 |
| Perfume | 0.4 |
| Ubichinone 10 | 0.1 |
| Ammonia, 25% | 1.0 |
| Ammonium chloride | 0.5 |
| Panthenol | 0.8 |
| Water | ad 100.00 |

The dyestuff combinations either oxidative or direct dyes of anionic and cationic characters were incorporated into this carrier, whereby the water content was reduced accordingly. The colorations were carried out on wool patches, strands of bleached human hair and natural human hair at a color level of 8 by application of a 1:1 mixture of an emulsion comprising the dyestuffs as given in the examples below and a 6% hydrogen peroxide solution (pH-value of the mixture: 9.8) with 30 minutes processing at room temperature, subsequent rinsing and drying.

The following colorations were obtained:

TABLE I

Examples 1 to 5

| | Example | | | | |
|---|---|---|---|---|---|
| | I | II | III | IV | V |
| | (all values are weight %) | | | | |
| p-phenylenediamine sulfate | 0.90 | 0.90 | 0.90 | 0.90 | 0.90 |
| □-naphtol | 0.63 | 0.63 | 0.63 | 0.63 | 0.63 |
| $R_9 = R_{10} = R_{11} = R_{12}$ = methyl and Y is chloride | 0.06 | 0.04 | 0.02 | 0.08 | — |
| Acid red 52 | 0.02 | 0.04 | 0.06 | — | 0.08 |

Examples I to III are according to the invention and examples IV and V are for comparative purposes.

The coloring compositions so obtained show excellent dyeing performance.

In order show color fastness (durability) against washing, all colored strands were washed 10 times under usual hair wash conditions with a commercial shampoo composition designed for colored hair of the trade mark Goldwell Definition, and color of the tresses (L, a and b values) were measured before and after shampooing optically with a laboratory equipment and color differences were calculated with the well known equation to obtain ΔE values and color intensity differences (ΔL) were obtained from measured L values. The results are presented in the Table II below.

TABLE II

| | Results of the durability test | | |
|---|---|---|---|
| Example | L1 | L2 | ΔE |
| I | 27.2 | 29 | 9.0 |
| II | 27.6 | 29.2 | 8.0 |
| III | 28.9 | 31.1 | 5.7 |
| IV | 28.3 | 34 | 14 |
| V | 29.0 | 32 | 12 |

L1 stands for the intensity of the color measured before the washing test and L2 is the same value measured after washing the strands 10 times with shampoo. ΔE value is obtained from the L, a and b values measured before and after washing. As it is obvious from the table immediately after coloring there is no real difference in the intensity though shade differences were obvious (not shown). However, after washing the strands with shampoo, intensity differences were obvious between the strands colored only with either cationic or anionic dyes (non inventive examples IV and V, respectively) and the strands colored with mixture of anionic and cationic dyes according to the present invention. This is furthermore expressed with ΔE values as the color difference.

The invention claimed is:

1. Coloring composition for keratin fibers, especially for hair characterized in that it comprises at least one acidic direct dye and at least one cationic direct dye selected from compounds presented with general formula

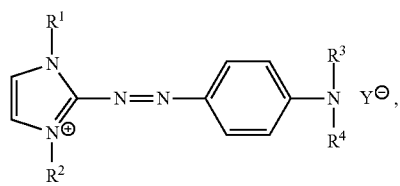
(I)

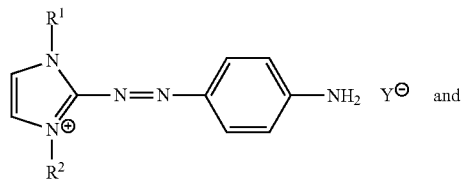
(II)

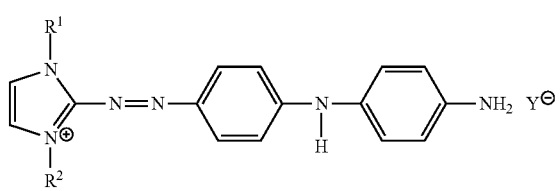
(III)

wherein $R^1$, $R^2$, $R^3$ and $R^4$ stand for hydrogen, a $CH_3$— or $C_2H_5$— group, and Y is an anion selected from the group consisting of chloride, bromide, and methosulfate.

2. Composition according to claim 1 characterized in that cationic dyestuff is

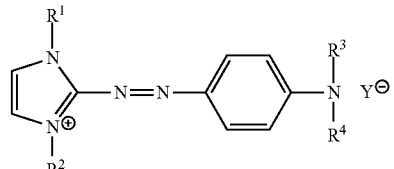

wherein $R^1$, $R^2$, $R^3$ and $R^4$ are $CH_3$— group, and Y is chloride.

3. Composition according to claim 1 characterized in that cationic dyestuff is

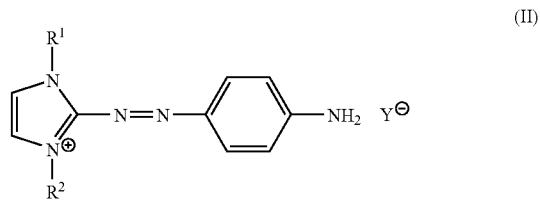
(II)

wherein $R^1$ and $R^2$ re $CH_3$— group, and Y is chloride.

4. Composition according to claim 1 characterized in that it comprises at least one anionic dyestuff selected from Acid Red 52, DC Violet 2, DC Red 33, DC Orange 4, DC Red 27 and DC Yellow 10.

5. Composition according to claim 1 characterized in that pH of the composition is between 5 and 12.

6. Composition according to claim 1 characterized in that pH of the composition is between 6.8 and 10.

7. Composition according to claim 1 characterized in that it comprises at least one cationic dyestuff and at least one acidic dyestuff at a weight ratio of 3:1 to 1:10.

8. Composition according to claim 1 characterized in that it comprises anionic direct dye at a concentration of 0.1-7.5% by weight, calculated to the total composition.

9. Composition according to claim 1 characterized in that it comprises cationic direct dye at a concentration of 0.01-2.5% by weight, calculated to the total composition.

10. Composition according to claim 1 characterized in that it comprises HC dyes in addition to anionic and cationic direct dyes.

11. Composition according to claim 1 characterized in that it comprises an additional cationic direct dye.

12. Composition according to claim 1 characterized in that it further comprises saturated and/or unsaturated fatty acids with 0 to 3 ethylenic bonds and a fatty acyl chain length of 12 to 22 C atoms.

13. Composition according to claim 12 characterized in that the fatty acid is oleic acid.

14. Composition according to claim 1 characterized in that it further comprises fatty alcohol and one or more surfactants selected from anionic, nonionic, amphoteric and/or cationic surfactants.

15. Composition according to claim 14 characterized in that anionic surfactants are selected from alkyl sulfates and alkyl ether sulfates, nonionic surfactants are selected from fatty acids mono or diethanolamides and fatty alcohols are with a fatty acyl chain length of 14 to 22 C atoms.

16. Composition according to claim 1 characterized in that it comprises organosiloxane polymer according to formula

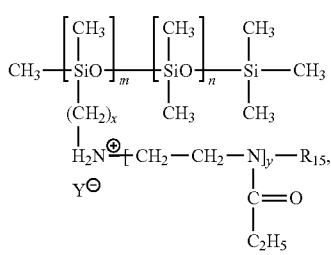

wherein m and n each are numbers from 20 to 10,000, x is a number between 1 and 5, and y is a number from 5 to 30, $R_{15}$ is a $C_1$-$C_{12}$-alkyl or aryl group, in particular a methyl, ethyl or benzyl group, and $Y^-$ is an anion.

17. Composition according to claim 1 characterized in that it comprises additionally ceramide type compound according to the formula

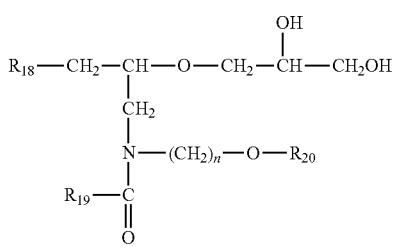

where $R_{18}$ and $R_{19}$ are independent from each other alkyl- or alkenyl group mit 10 to 22 carbon atoms, $R_{20}$ is methyl, ethyl, n-propyl or isopropyl group and n is a number between 1 to 6.

18. Composition according to claim 1 characterized in that it comprises additionally organic solvents.

19. Composition according to claim 1 characterized in that it comprises additionally UV absorbers selected from anionic water soluble ones and/or nonionic oil soluble ones.

20. Composition according to claim 1 characterized in that it is mixed with a composition comprising at least one oxidizing agent prior to application onto hair at a weight ratio of 4:1 to 1:4.

21. Composition according claim 20 characterized in that oxidizing agent is hydrogen peroxide at a concentration of 3 to 12% by weight calculated to total composition.

22. Composition according to claim 20 characterized in that it comprises additionally oxidative dyes precursors and coupling substances.

23. Process for colouring and lightening hair characterised in that a composition according to claim 20 is applied onto hair and left 5 to 45 min and rinsed off from hair.

24. Process for colouring and lightening hair characterised in that an oxidizing composition comprising at least one oxidizing agent is applied onto dry hair and left for 5 to 45 min on hair and without rinsing it off from hair a colouring composition according to claim 1 is applied onto hair and left further for 5 to 45 min on hair and rinsed off form hair.

25. Process according to claim 24 characterised in that before application of colouring composition oxidizing agent is rinsed off from hair and hair dried and subsequently a colouring composition according to claim 1is applied onto hair and left further for 5 to 45 min on hair and rinsed off form hair.

26. Coloring composition for keratin fibers, especially for hair characterised in that it comprises at least one acidic direct dye and at least one cationic direct dye selected from compounds presented with general formula

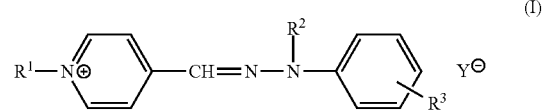

wherein $R^1$ and $R^2$ stand for hydrogen, a $CH_3$— or $C_2H_5$— group, $R^3$ stands for hydrogen, —$OCH_3$ or —$OC_2H_5$, and $Y^-$ is selected from the group consisting of chloride, bromide, methosulfate.

27. Process for colouring and lightening hair characterised in that an oxidizing composition comprising at least one oxidizing agent is applied onto dry hair and left for 5 to 45 min on hair and without rinsing it off from hair a colouring composition according to claim 1 is applied onto hair and left further for 5 to 45 min on hair and rinsed off form hair.

28. Composition for the dyeing of keratin fibers, especially human hair, characterized in that it comprises a) at least one oxidation dye precursor selected from selected from pyrazole or the water-soluble salts thereof, b) at least one acidic direct dye, and c) at least one cationic direct dye selected from the compounds presented with the general formulas III, IV, V and VI

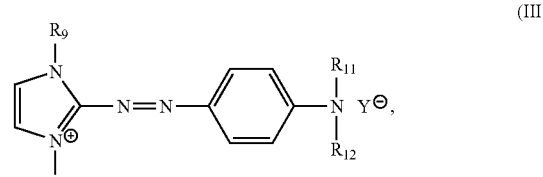

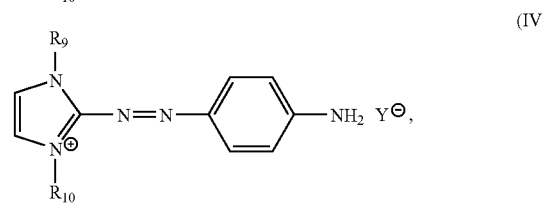

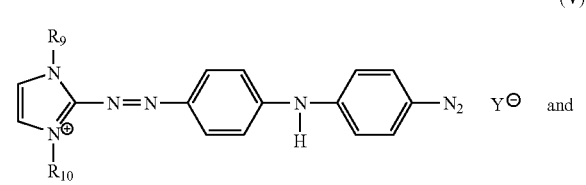

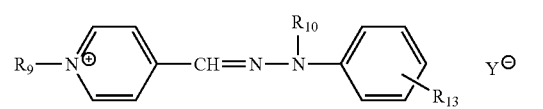

wherein $R_9$, $R_{10}$, $R_{11}$ and $R_{12}$ is selected from hydrogen, a $CH_3$— or $C_2H_5$— group, $R_{13}$ is selected from hydrogen, —$OCH_3$ or —$OC_2H_5$ and Y is an anion selected from the group consisting of chloride, bromide, and methosulfate.

29. Composition for the dyeing of keratin fibers, especially human hair, characterized in that it comprises
- a) At least one oxidation dye precursor selected from tetraminopyrimidines, triaminohydroxypyrimidines, diamino mono- and -di-hydroxy-pyrimidines and/or aminotriazines or water-soluble salts thereof,
- b) at least one acidic direct dye, and
- c) at least one cationic direct dye selected from the compounds presented with the general formulas III, IV, V and VI

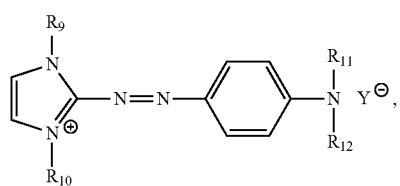
(III)

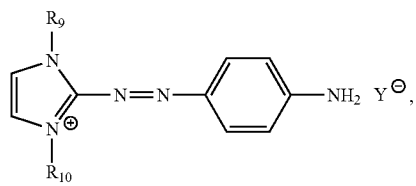
(IV)

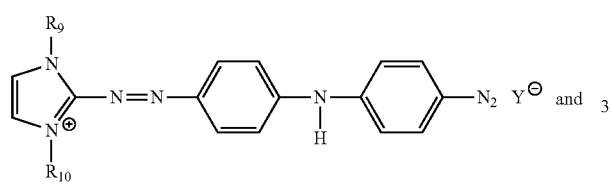
(V)

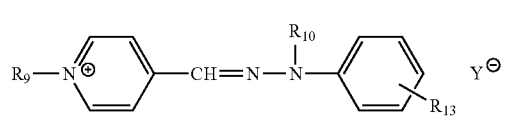
(VI)

wherein $R_9$, $R_{10}$, $R_{11}$ and $R_{12}$ selected from hydrogen, a $CH_3$— or $C_2H_5$— group, $R_{13}$ selected from hydrogen, —$OCH_3$ or —$OC_2H_5$ and Y is an anion selected from the group consisting of chloride, bromide, and methosulfate.

30. Composition for the dyeing of keratin fibers, especially human hair, characterized in that it comprises
- a) At least one oxidation dye precursor selected from tetraminopyrimidines, triaminohydroxypyrimidines, diamino mono- and -di-hydroxy-pyrimidines and/or aminotriazines or water-soluble salts thereof,
- b) at least one acidic direct dye, and
- c) at least one cationic direct dye selected from the compounds presented with the general formulas III, IV, V and VI

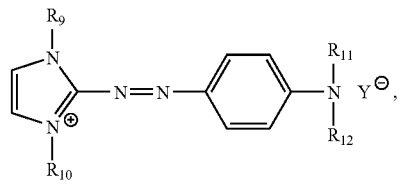
(III)

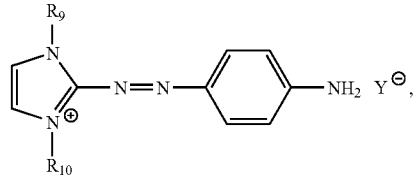
(IV)

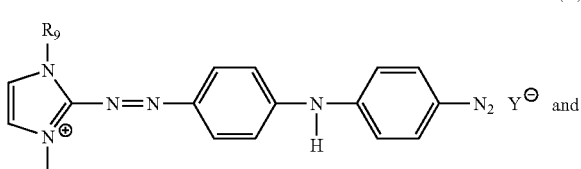
(V)

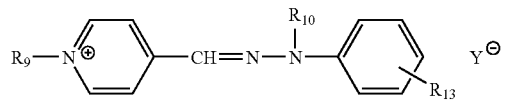
(VI)

wherein $R_9$, $R_{10}$, $R_{11}$ and $R_{12}$ selected from hydrogen, a $CH_3$— or $C_2H_5$— group, $R_{13}$ selected from hydrogen, —$OCH_3$ or —$OC_2H_5$ and Y is an anion selected from the group consisting of chloride, bromide, and methosulfate.

* * * * *